(12) United States Patent
Ikeda et al.

(10) Patent No.: US 7,839,074 B2
(45) Date of Patent: Nov. 23, 2010

(54) ORGANIC ELECTROLUMINESCENCE DEVICE AND ANTHRACENE DERIVATIVE

(75) Inventors: Hidetsugu Ikeda, Sodegaura (JP); Motohisa Ido, Sodegaura (JP); Masakazu Funahashi, Sodegaura (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 192 days.

(21) Appl. No.: 10/524,825

(22) PCT Filed: Aug. 18, 2003

(86) PCT No.: PCT/JP03/10402

§ 371 (c)(1),
(2), (4) Date: Feb. 18, 2005

(87) PCT Pub. No.: WO2004/018587

PCT Pub. Date: Mar. 4, 2004

(65) Prior Publication Data

US 2006/0043858 A1    Mar. 2, 2006

(30) Foreign Application Priority Data

Aug. 23, 2002  (JP) ............................. 2002-243545

(51) Int. Cl.
*H01L 51/54*  (2006.01)
*H05B 33/14*  (2006.01)
*C09K 11/06*  (2006.01)
*C07C 13/48*  (2006.01)

(52) U.S. Cl. ........................ 313/504; 313/506; 428/690; 428/917; 585/26; 252/301.16

(58) Field of Classification Search ........................ None
See application file for complete search history.

(56) References Cited

U.S. PATENT DOCUMENTS

| | | | | |
|---|---|---|---|---|
| 5,935,721 | A * | 8/1999 | Shi et al. ..................... | 428/690 |
| 5,972,247 | A * | 10/1999 | Shi et al. ..................... | 252/583 |
| 6,713,192 | B2 | 3/2004 | Fukuoka et al. | |
| 6,929,870 | B2 | 8/2005 | Ishida et al. | |
| 6,998,487 | B2 | 2/2006 | Kim et al. | |
| 7,169,482 | B2 | 1/2007 | Aziz et al. | |
| 2001/0051285 | A1* | 12/2001 | Shi et al. ..................... | 428/690 |
| 2002/0028346 | A1* | 3/2002 | Shi et al. ..................... | 428/690 |
| 2004/0018380 | A1 | 1/2004 | Aziz et al. | |
| 2005/0233165 | A1 | 10/2005 | Ido et al. | |
| 2007/0114542 | A1 | 5/2007 | Yamazaki et al. | |

FOREIGN PATENT DOCUMENTS

| | | |
|---|---|---|
| EP | 0 952 200 A2 | 10/1999 |
| EP | 1 009 044 A2 | 8/2000 |
| EP | 1 167 488 A1 | 1/2002 |
| EP | 1 221 434 A1 | 7/2002 |
| EP | 1 333 018 A1 | 8/2003 |
| JP | 3-200889 | 9/1991 |
| JP | 7-138561 | 5/1995 |
| JP | 8-12600 | 1/1996 |
| JP | 08-199162 | 8/1996 |
| JP | 8-239655 | 9/1996 |
| JP | 2000-182776 | 6/2000 |
| JP | 2000-273056 | 10/2000 |
| JP | 2000-344691 | 12/2000 |
| JP | 2001-052870 | 2/2001 |
| JP | 2001-196179 | 7/2001 |
| JP | 2001-223082 | 8/2001 |
| JP | 2001-257074 | 9/2001 |
| JP | 2001-284050 | 10/2001 |
| JP | 2002-124385 | 4/2002 |
| JP | 2002-154993 | 5/2002 |
| JP | 2003-128651 | 5/2003 |
| JP | 2003-229273 | 8/2003 |
| JP | 2003-261472 | 9/2003 |
| JP | 2003-338377 | 11/2003 |
| JP | 2004-042485 | 2/2004 |
| JP | 2004-059535 | 2/2004 |
| JP | 2004-079421 | 3/2004 |

OTHER PUBLICATIONS

JP 2001-097897, Ikeda et al., Machine Translation.*
Patent Abstracts of Japan, 2002-329580, Nov. 15, 2002.
Patent Abstracts of Japan, 2001-223082, Aug. 17, 2001.
Patent Abstracts of Japan, 10-294179, Nov. 4, 1998.
Patent Abstracts of Japan, 11-003782, Jan. 6, 1999.
C. W. Tang, et al. "Organic electroluminescent diodes" Appl. Phys. Lett. vol. 51, Sep. 1987, American Institute of Physics, pp. 913-915.

* cited by examiner

*Primary Examiner*—D. Lawrence Tarazano
*Assistant Examiner*—Brett A Crouse
(74) *Attorney, Agent, or Firm*—Oblon, Spivak, McClelland, Maier & Neustadt, L.L.P.

(57) ABSTRACT

An organic electroluminescence device which comprises a cathode, an anode and an organic thin film layer comprising at least one layer comprising a light emitting layer and disposed between the cathode and the anode, wherein at least one layer in the organic thin film layer comprises an anthracene derivative having a specific structure singly or as a component of a mixture, and an anthracene derivative having a specific asymmetric structure and providing an organic electroluminescence device exhibiting a great efficiency of light emission and having a long life, are provided.

7 Claims, No Drawings

ORGANIC ELECTROLUMINESCENCE DEVICE AND ANTHRACENE DERIVATIVE

TECHNICAL FIELD

The present invention relates to an organic electroluminescence device and an anthracene derivative and, more particularly, to an electroluminescence device exhibiting a great efficiency of light emission and having a long life and an anthracene derivative providing the device.

BACKGROUND ART

An organic electroluminescence ("electroluminescence" will be occasionally referred to as "EL", hereinafter) device is a spontaneous light emitting device which utilizes the principle that a fluorescent substance emits light by energy of recombination of holes injected from an anode and electrons injected from a cathode when an electric field is applied. Since an organic EL device of the laminate type driven under a low electric voltage was reported by C. W. Tang of Eastman Kodak Company (C. W. Tang and S. A. Vanslyke, Applied Physics Letters, Volume 51, Pages 913, 1987), many studies have been conducted on organic EL devices using organic materials as the constituting materials. Tang et al. used a laminate structure using tris(8-hydroxyquinolinol)aluminum for the light emitting layer and a triphenyldiamine derivative for the hole transporting layer. Advantages of the laminate structure are that the efficiency of hole injection into the light emitting layer can be increased, that the efficiency of forming excited particles which are formed by blocking and recombining electrons injected from the cathode can be increased, and that excited particles formed within the light emitting layer can be enclosed. As the structure of the organic EL device, a two-layered structure having a hole transporting (injecting) layer and an electron transporting and light emitting layer and a three-layered structure having a hole transporting (injecting) layer, a light emitting layer and an electron transporting (injecting) layer are well known. To increase the efficiency of recombination of injected holes and electrons in the devices of the laminate type, the structure of the device and the process for forming the device have been studied.

As the light emitting material, chelate complexes such as tris(8-quinolinolato)aluminum, coumarine derivatives, tetraphenyl-butadiene derivatives, bisstyrylarylene derivatives and oxadiazole derivatives are known. It is reported that light in the visible region ranging from blue light to red light can be obtained by using these light emitting materials, and development of a device exhibiting color images is expected (For example, Japanese Patent Application Laid-Open Nos. Heisei 8(1996)-239655, Heisei 7(1995)-138561 and Heisei 3(1991)-200289).

A device using a phenylanthracene derivative as the light emitting material is disclosed in Japanese Patent Application Laid-Open No. Heisei 8(1996)-012600. This anthracene derivative is used as the material for emitting bluish light, but an increase in the life of the device have been desired. A compound having fluoranthene group at the 9- and 10-positions of anthracene is disclosed as the material for the device in Japanese Patent Application Laid-Open No. 2001-257074. This compound is also used as the material for emitting bluish light, but an increase in the life of the device have also been desired. It is disclosed in Japanese Patent Application Laid-Open No. 2000-182776 that various anthracene derivatives are used as the hole transporting material. However, these derivatives have not been actually synthesized, and the evaluation of these compounds as the light emitting material has not been made.

DISCLOSURE OF THE INVENTION

The present invention has been made to overcome the above problems and has an object of providing an EL device exhibiting a great efficiency of light emission and has a long life and an anthracene derivative providing the device.

As the result of intensive studies by the present inventors to achieve the above object, it was found that an EL device exhibiting a great efficiency of light emission and has a long life could be obtained when a compound having an anthracene structure having a specific asymmetric structure represented by general formula (1) or (2) shown below is used as the light emitting material of an organic EL device. The present invention has been completed based on this knowledge.

The present invention provides an organic electroluminescence device which comprises a cathode, an anode and an organic thin film layer comprising at least one layer comprising a light emitting layer and disposed between the cathode and the anode, wherein at least one layer in the organic thin film layer comprises, singly or as a component of a mixture, an anthracene derivative represented by general formula (1) or (2) shown in the following.

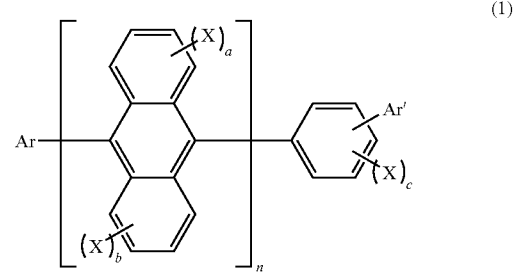

(1)

In general formula (1), Ar represents a substituted or unsubstituted condensed aromatic group having 10 to 50 nuclear carbon atoms;

Ar' represents a substituted or unsubstituted aromatic group having 6 to 50 nuclear carbon atoms;

X represents a substituted or unsubstituted aromatic group having 6 to 50 nuclear carbon atoms, a substituted or unsubstituted aromatic heterocyclic group having 5 to 50 nuclear atoms, a substituted or unsubstituted alkyl group having 1 to 50 carbon atoms, a substituted or unsubstituted alkoxyl group having 1 to 50 carbon atoms, a substituted or unsubstituted aralkyl group having 6 to 50 carbon atoms, a substituted or unsubstituted aryloxyl group having 5 to 50 nuclear atoms, a substituted or unsubstituted arylthio group having 5 to 50 nuclear atoms, a substituted or unsubstituted alkoxycarbonyl group having 1 to 50 carbon atoms, carboxyl group, a halogen atom, cyano group, nitro group or hydroxyl group;

a, b and c each represent an integer of 0 to 4; and n represents an integer of 1 to 3 and, when n represents 2 or 3, a plurality of groups in [ ] represented by:

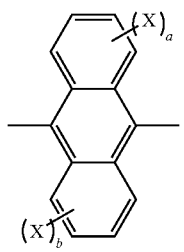

may be a same with or different from each other.

The present invention also provides an anthracene derivative represented by following general formula (2):

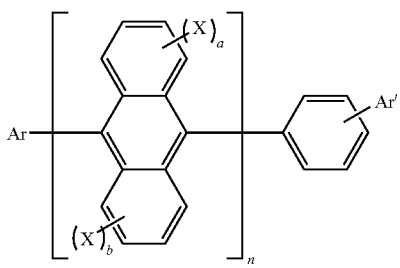

wherein Ar represents a substituted or unsubstituted condensed aromatic group having 10 to 50 nuclear carbon atoms;

Ar' represents a substituted or unsubstituted aromatic group having 6 to 50 nuclear carbon atoms;

X represents a substituted or unsubstituted aromatic group having 6 to 50 nuclear carbon atoms, a substituted or unsubstituted aromatic heterocyclic group having 5 to 50 nuclear atoms, a substituted or unsubstituted alkyl group having 1 to 50 carbon atoms, a substituted or unsubstituted alkoxyl group having 1 to 50 carbon atoms, a substituted or unsubstituted aralkyl group having 6 to 50 carbon atoms, a substituted or unsubstituted aryloxyl group having 5 to 50 nuclear atoms, a substituted or unsubstituted arylthio group having 5 to 50 nuclear atoms, a substituted or unsubstituted alkoxycarbonyl group having 1 to 50 carbon atoms, carboxyl group, a halogen atom, cyano group, nitro group or hydroxyl group;

a and b each represent an integer of 0 to 4; and n represents an integer of 1 to 3 and, when n represents 2 or 3, a plurality of groups in [ ] represented by:

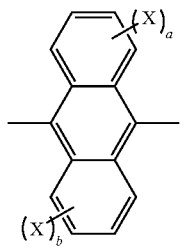

may be a same with or different from each other.

THE MOST PREFERRED EMBODIMENT TO CARRY OUT THE INVENTION

The organic EL device of the present invention comprises a cathode, an anode and an organic thin film layer comprising at least one layer comprising a light emitting layer and disposed between the cathode and the anode, wherein at least one layer in the organic thin film layer comprises an anthracene derivative represented by general formula (1) shown above singly or as a component of a mixture.

In general formula (1), Ar represents a substituted or unsubstituted condensed aromatic group having 10 to 50 nuclear carbon atoms.

Examples of the condensed aromatic group include 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 3-methyl-2-naphthyl group, 4-methyl-1-naphthyl group and 4-methyl-1-anthryl group.

It is preferable that the group represented by Ar in general formula (1) is a group selected from groups represented by following general formulae:

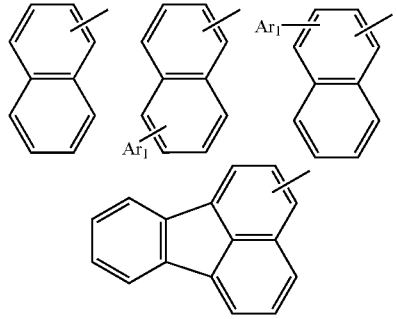

wherein $Ar_1$ represents a substituted or unsubstituted aromatic group having 6 to 50 nuclear carbon atoms.

Examples of the group represented by $Ar_1$ include phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group and 4"-t-butyl-p-terphenyl-4-yl group.

In general formula (1), Ar' represents a substituted or unsubstituted aromatic group having 6 to 50 nuclear carbon atoms. Examples of the aromatic group include phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group and 4"-t-butyl-p-terphenyl-4-yl group.

Among these groups, substituted and substituted aromatic groups having 10 or more nuclear carbon atoms such as 1-naphthyl group, 2-naphthyl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, o-tolyl group, m-tolyl group, p-tolyl group and p-t-butylphenyl group are preferable.

In general formula (1), X represents a substituted or unsubstituted aromatic group having 6 to 50 nuclear carbon atoms, a substituted or unsubstituted aromatic heterocyclic group having 5 to 50 nuclear atoms, a substituted or unsubstituted alkyl group having 1 to 50 carbon atoms, a substituted or unsubstituted alkoxyl group having 1 to 50 carbon atoms, a substituted or unsubstituted aralkyl group having 6 to 50 carbon atoms, a substituted or unsubstituted aryloxyl group having 5 to 50 nuclear atoms, a substituted or unsubstituted arylthio group having 5 to 50 nuclear atoms, a substituted or unsubstituted alkoxycarbonyl group having 1 to 50 carbon atoms, carboxyl group, a halogen atom, cyano group, nitro group or hydroxyl group.

Examples of the substituted and unsubstituted aromatic group represented by X include phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl-group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methyl-biphenylyl group and 4"-t-butyl-p-terphenyl-4-yl group.

Examples of the substituted and unsubstituted aromatic heterocyclic group represented by X include 1-pyrrolyl group, 2-pyrrolyl group, 3-pyrrolyl group, pyradinyl group, 2-pyridinyl group, 3-pyridinyl group, 4-pyridinyl group, 1-indolyl group, 2-indolyl group, 3-indolyl group, 4-indolyl group, 5-indolyl group, 6-indolyl group, 7-indolyl group, 1-isoindolyl group, 2-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, 2-quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl group, 5-quinoxalinyl group, 6-quinoxalinyl group, 1-carbazolyl group, 2-carbazolyl group, 3-carbazolyl group, 4-carbazolyl group, 9-carbazolyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthrolin-2-yl group, 1,7-phenanthrolin-3-yl group, 1,7-phenanthrolin-4-yl group, 1,7-phenanthrolin-5-yl group, 1,7-phenanthrolin-6-yl group, 1,7-phenanthrolin-8-yl group, 1,7-phenanthrolin-9-yl group, 1,7-phenanthrolin-10-yl group, 1,8-phenanthrolin-2-yl group, 1,8-phenanthrolin-3-yl group, 1,8-phenanthrolin-4-yl group, 1,8-phenanthrolin-5-yl group, 1,8-phenanthrolin-6-yl group, 1,8-phenanthrolin-7-yl group, 1,8-phenanthrolin-9-yl group, 1,8-phenanthrolin-10-yl group, 1,9-phenanthrolin-2-yl group, 1,9-phenanthrolin-3-yl group, 1,9-phenanthrolin-4-yl group, 1,9-phenanthrolin-5-yl group, 1,9-phenanthrolin-6-yl group, 1,9-phenanthrolin-7-yl group, 1,9-phenanthrolin-8-yl group, 1,9-phenanthrolin-10-yl group, 1,10-phenanthrolin-2-yl group, 1,10-phenanthrolin-3-yl group, 1,10-phenanthrolin-4-yl group, 1,10-phenanthrolin-5-yl group, 2,9-phenanthrolin-1-yl group, 2,9-phenanthrolin-3-yl group, 2,9-phenanthrolin-4-yl group, 2,9-phenanthrolin-5-yl group, 2,9-phenanthrolin-6-yl group, 2,9-phenanthrolin-7-yl group, 2,9-phenanthrolin-8-yl group, 2,9-phenanthrolin-10-yl group, 2,8-phenanthrolin-1-yl group, 2,8-phenanthrolin-3-yl group, 2,8-phenanthrolin-4-yl group, 2,8-phenanthrolin-5-yl group, 2,8-phenanthrolin-6-yl group, 2,8-phenanthrolin-7-yl group, 2,8-phenanthrolin-9-yl group, 2,8-phenanthrolin-10-yl group, 2,7-phenanthrolin-1-yl group, 2,7-phenanthrolin-3-yl group, 2,7-phenanthrolin-4-yl group, 2,7-phenanthrolin-5-yl group, 2,7-phenanthrolin-6-yl group, 2,7-phenanthrolin-8-yl group, 2,7-phenanthrolin-9-yl group, 2,7-phenanthrolin-10-yl group, 1-phenazinyl group, 2-phenazinyl group, 1-phenothiazinyl group, 2-phenothiazinyl group, 3-phenothiazinyl group, 4-phenothiazinyl group, 10-phenothiazinyl group, 1-phenoxazinyl group, 2-phenoxazinyl group, 3-phenoxazinyl group, 4-phenoxazinyl group, 10-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrol-1-yl group, 2-methylpyrrol-3-yl group, 2-methylpyrrol-4-yl group, 2-methyl-pyrrol-5-yl group, 3-methylpyrrol-1-yl group, 3-methylpyrrol-2-yl group, 3-methylpyrrol-4-yl group, 3-methylpyrrol-5-yl group, 2-t-butylpyrrol-4-yl group, 3-(2-phenylpropyl)pyrrol-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group and 4-t-butyl-3-indolyl group.

Examples of the substituted and unsubstituted alkyl group represented by X include methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydroxyethyl group, 1,3-dihydroxy-isopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triamino-propyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 2-nitroisobutyl group, 1,2-dinitroethyl group, 1,3-dinitroisopropyl group, 2,3-dinitro-t-butyl group, 1,2,3-trinitropropyl group, cyclopropyl group, cyclobutyl group, cyclopentyl group, cyclohexyl group, 4-methylcyclohexyl group, 1-adamantyl group, 2-adamantyl group, 1-norbornyl group and 2-norbornyl group.

The substituted and unsubstituted alkoxyl group represented by X is a group represented by —OY. Examples of the group represented by Y include methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydroxyethyl group, 1,3-dihydroxy-isopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 2-nitroisobutyl group, 1,2-dinitro-ethyl group, 1,3-dinitroisopropyl group, 2,3-dinitro-t-butyl group and 1,2,3-trinitropropyl group.

Examples of the substituted and unsubstituted aralkyl group represented by X include benzyl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthyl-isopropyl group, β-naphthylmethyl group, 1-β-naphthylethyl group, 2-β-naphthylethyl group, 1-β-naphthylisopropyl group, 2-β-naphthyl-isopropyl group, 1-pyrrolylmethyl group, 2-(1-pyrrolyl)ethyl group, p-methylbenzyl group, m-methylbenzyl group, o-methylbenzyl group, p-chlorobenzyl group, m-chlorobenzyl group, o-chlorobenzyl group, p-bromobenzyl group, m-bromobenzyl group, o-bromobenzyl group, p-iodobenzyl group, m-iodobenzyl group, o-iodobenzyl group, p-hydroxybenzyl group, m-hydroxybenzyl group, o-hydroxybenzyl group, p-aminobenzyl group, m-aminobenzyl group, o-aminobenzyl group, p-nitrobenzyl group, m-nitrobenzyl group, o-nitrobenzyl group, p-cyanobenzyl group, m-cyanobenzyl group, o-cyanobenzyl group, 1-hydroxy-2-phenylisopropyl group and 1-chloro-2-phenylisopropyl group.

The substituted and unsubstituted aryloxyl group represented by X is a group represented by —OY'. Examples of the group represented by Y' include phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, 4"-t-butyl-p-terphenyl-4-yl group, 2-pyrrolyl-group, 3-pyrrolyl group, pyradinyl group, 2-pyridinyl group, 3-pyridinyl group, 4-pyridinyl group, 2-indolyl group, 3-indolyl group, 4-indolyl group, 5-indolyl group, 6-indolyl group, 7-indolyl group, 1-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, 2-quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxanyl group, 5-quinoxanyl group, 6-quinoxanyl group, 1-carbazolyl group, 2-carbazolyl group, 3-carbazolyl group, 4-carbazolyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthrolin-2-yl group, 1,7-phenanthrolin-3-yl group, 1,7-phenanthrolin-4-yl group, 1,7-phenanthrolin-5-yl group, 1,7-phenanthrolin-6-yl group, 1,7-phenanthrolin-8-yl group, 1,7-phenanthrolin-9-yl group, 1,7-phenanthrolin-10-yl group, 1,8-phenanthrolin-2-yl group, 1,8-phenanthrolin-3-yl group, 1,8-phenanthrolin-4-yl group, 1,8-phenanthrolin-5-yl group, 1,8-phenanthrolin-6-yl group, 1,8-phenanthrolin-7-yl group, 1,8-phenanthrolin-9-yl group, 1,8-phenanthrolin-10-yl group, 1,9-phenanthrolin-2-yl group, 1,9-phenanthrolin-3-yl group, 1,9-phenanthrolin-4-yl group, 1,9-phenanthrolin-5-yl group, 1,9-phenanthrolin-6-yl group, 1,9-phenanthrolin-7-yl group, 1,9-phenanthrolin-8-yl group, 1,9-phenanthrolin-10-yl group, 1,10-phenanthrolin-2-yl group, 1,10-phenanthrolin-3-yl group, 1,10-phenanthrolin-4-yl group, 1,10-phenanthrolin-5-yl group, 2,9-phenanthrolin-1-yl group, 2,9-phenanthrolin-3-yl group, 2,9-phenanthrolin-4-yl group, 2,9-phenanthrolin-5-yl group, 2,9-phenanthrolin-6-yl group, 2,9-phenanthrolin-7-yl group, 2,9-phenanthrolin-8-yl group, 2,9-phenanthrolin-10-yl group, 2,8-phenanthrolin-1-yl group, 2,8-phenanthrolin-3-yl group, 2,8-phenanthrolin-4-yl group, 2,8-phenanthrolin-5-yl group, 2,8-phenanthrolin-6-yl group, 2,8-phenanthrolin-7-yl group, 2,8-phenanthrolin-9-yl group, 2,8-phenanthrolin-10-yl group, 2,7-phenanthrolin-1-yl group, 2,7-phenanthrolin-3-yl group, 2,7-phenanthrolin-4-yl group, 2,7-phenanthrolin-5-yl group, 2,7-phenanthrolin-6-yl group, 2,7-phenanthrolin-8-yl group, 2,7-phenanthrolin-9-yl group, 2,7-phenanthrolin-10-yl group, 1-phenazinyl group, 2-phenazinyl group, 1-phenothiazinyl group, 2-phenothiazinyl group, 3-phenothiazinyl group, 4-phenothiazinyl group, 1-phenoxazinyl group, 2-phenoxazinyl group, 3-phenoxazinyl group, 4-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrol-1-yl group, 2-methylpyrrol-3-yl group, 2-methylpyrrol-4-yl group, 2-methylpyrrol-5-yl group, 3-methylpyrrol-1-yl group, 3-methyl-pyrrol-2-yl group, 3-methylpyrrol-4-yl group, 3-methylpyrrol-5-yl group, 2-t-butylpyrrol-4-yl group, 3-(2-phenylpropyl)pyrrol-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group and 4-t-butyl-3-indolyl group.

The substituted and unsubstituted arylthio group represented by X is a group represented by —SY". Examples of the group represented by Y" include phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, 4"-t-butyl-p-terphenyl-4-yl group, 2-pyrrolyl group, 3-pyrrolyl group, pyradinyl group, 2-pyridinyl group, 3-pyridinyl group, 4-pyridinyl group, 2-indolyl group, 3-indolyl group, 4-indolyl group, 5-indolyl group, 6-indolyl group, 7-indolyl group, 1-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, 2-quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl group, 5-quinoxalinyl group, 6-quinoxalinyl group, 1-carbazolyl group, 2-carbazolyl group, 3-carbazolyl group, 4-carbazolyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthrolin-2-yl group, 1,7-phenanthrolin-3-yl group, 1,7-phenanthrolin-4-yl group, 1,7-phenanthrolin-5-yl group, 1,7-phenanthrolin-6-yl group, 1,7-phenanthrolin-8-yl group, 1,7-phenanthrolin-9-yl group, 1,7-phenanthrolin-10-yl group, 1,8-phenanthrolin-2-yl group, 1,8-phenanthrolin-3-yl group, 1,8-phenanthrolin-4-yl group, 1,8-phenanthrolin-5-yl group, 1,8-phenanthrolin-6-yl group, 1,8-phenanthrolin-7-yl group, 1,8-phenanthrolin-9-yl group, 1,8-phenanthrolin-10-yl group, 1,9-phenanthrolin-2-yl group, 1,9-phenanthrolin-3-yl group, 1,9-phenanthrolin-4-yl group, 1,9-phenanthrolin-5-yl group, 1,9-phenanthrolin-6-yl group, 1,9-phenanthrolin-7-yl group, 1,9-phenanthrolin-8-yl group, 1,9-phenanthrolin-10-yl group, 1,10-phenanthrolin-2-yl group, 1,10-phenanthrolin-3-yl group, 1,10-phenanthrolin-4-yl group, 1,10-phenanthrolin-5-yl group, 2,9-phenanthrolin-1-yl group, 2,9-phenanthrolin-3-yl group, 2,9-phenanthrolin-4-yl group, 2,9-phenanthrolin-5-yl group, 2,9-phenanthrolin-6-yl group, 2,9-phenanthrolin-7-yl group, 2,9-phenanthrolin-8-yl group, 2,9-phenanthrolin-10-yl group, 2,8-phenanthrolin-1-yl group, 2,8-phenanthrolin-3-yl group, 2,8-phenanthrolin-4-yl group, 2,8-phenanthrolin-5-yl group, 2,8-phenanthrolin-6-yl group, 2,8-phenanthrolin-7-yl group, 2,8-phenanthrolin-9-yl group, 2,8-phenanthrolin-10-yl group, 2,7-phenanthrolin-1-yl group, 2,7-phenanthrolin-3-yl group, 2,7-phenanthrolin-4-yl group, 2,7-phenanthrolin-5-yl group, 2,7-phenanthrolin-6-yl group, 2,7-phenanthrolin-8-yl group, 2,7-phenanthrolin-9-yl group, 2,7-phenanthrolin-10-yl group, 1-phenazinyl group, 2-phenazinyl group, 1-phenothiazinyl group, 2-phenothiazinyl group, 3-phenothiazinyl group, 4-phenothiazinyl group, 1-phenoxazinyl group, 2-phenoxazinyl group, 3-phenoxazinyl group, 4-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrol-1-yl group, 2-methylpyrrol-3-yl group, 2-methylpyrrol-4-yl group, 2-methylpyrrol-5-yl group, 3-methylpyrrol-1-yl group, 3-methyl-pyrrol-2-yl group, 3-methylpyrrol-4-yl group, 3-methylpyrrol-5-yl group, 2-t-butylpyrrol-4-yl group, 3-(2-phenylpropyl)pyrrol-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group and 4-t-butyl-3-indolyl group.

The substituted and unsubstituted alkoxycarbonyl group represented by X is a group represented by —COOZ. Examples of the group represented by Z include methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydroxyethyl group, 1,3-dihydroxy-isopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triamino-propyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 2-nitroisobutyl group, 1,2-dinitro-ethyl group, 1,3-dinitroisopropyl group, 2,3-dinitro-t-butyl group and 1,2,3-trinitropropyl group.

Examples of the divalent group forming a ring include tetramethylene group, pentamethylene group, hexamethylene group, diphenylmethan-2,2'-diyl group, diphenylethan-3,3'-diyl group and diphenylpropan-4,4'-diyl group.

Examples of the halogen atom include fluorine, chlorine, bromine and iodine.

In general formula (1), a, b and c each represent an integer of 0 to 4 and preferably 0 or 1.

n represents an integer of 1 to 3 and, when n represents 2 or 3, the plurality of groups in [ ] may be the same with or different from each other.

Examples of the substituent in the groups represented by Ar, Ar' and X include halogen atoms, hydroxyl group, nitro group, cyano group, alkyl groups, aryl groups, cycloalkyl groups, alkoxyl groups, aromatic heterocyclic groups, aralkyl groups, aryloxyl groups, arylthio groups, alkoxycarbonyl groups and carboxyl group.

Examples of the anthracene derivative represented by general formula (1) of the present invention are shown in the following. However, the anthracene derivative represented by general formula (1) is not limited to the compounds shown as the examples. In the following formulae, Me represents methyl group, and Bu represents butyl group.

Among the anthracene derivatives represented by general formula (1), compounds represented by general formula (1) in which Ar and Ar' both represent naphthyl group and a=b=c=0 are preferable.

AN1
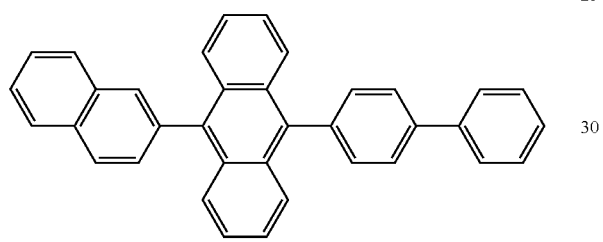

AN2
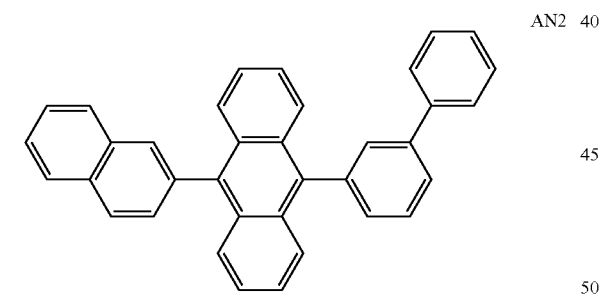

AN3
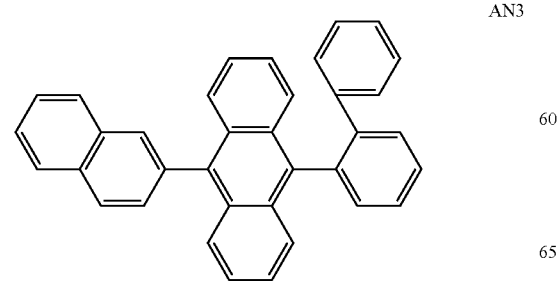

AN4
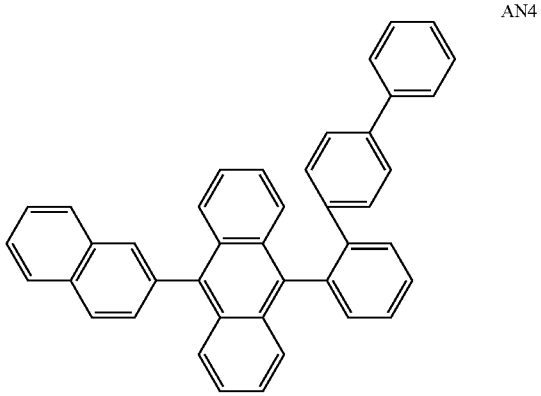

AN5
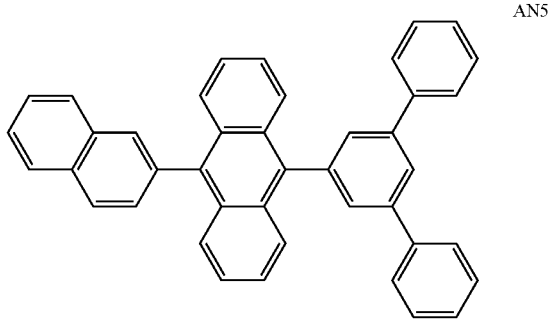

AN6
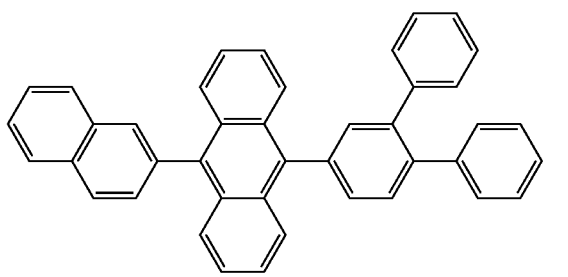

AN7
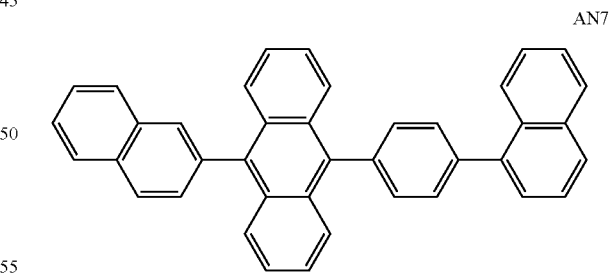

AN8
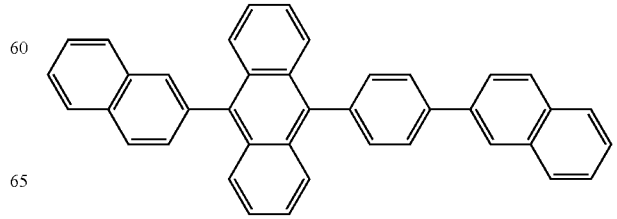

-continued
AN9
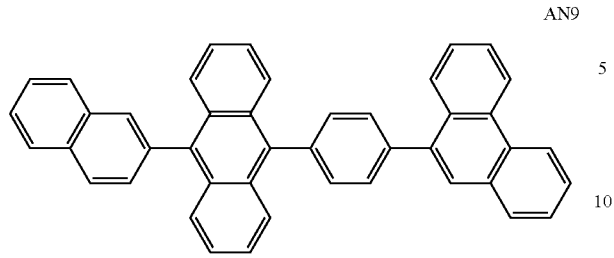
AN10
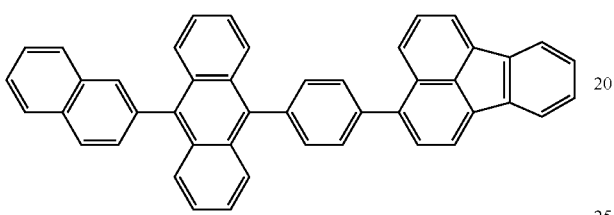
AN11
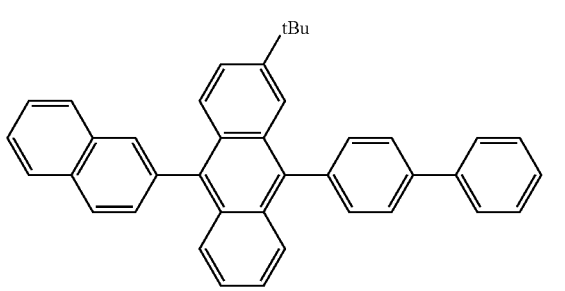
AN12
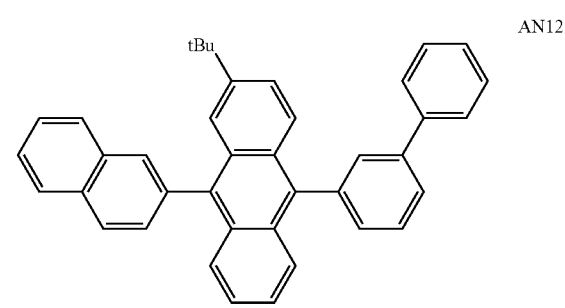
AN13
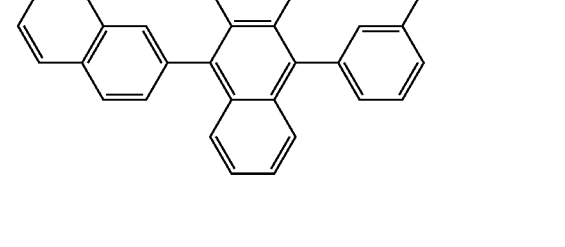
-continued
AN14
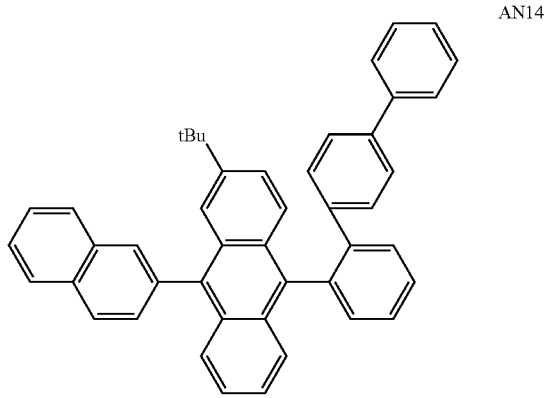
AN15
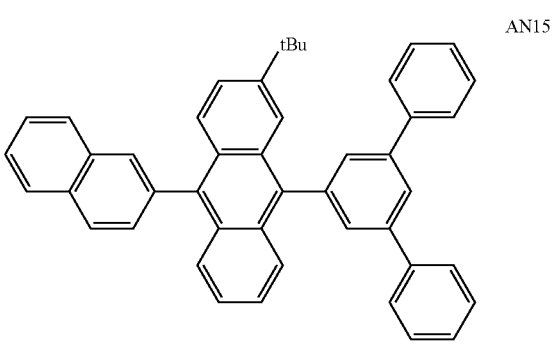
AN16
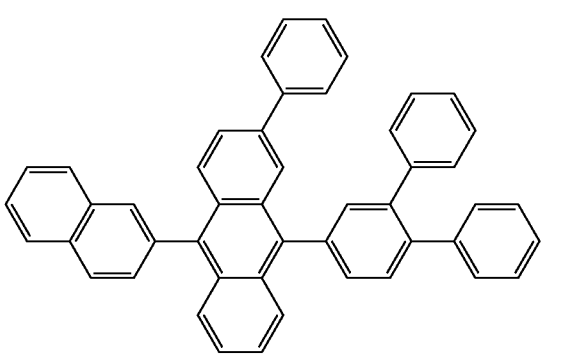
AN17
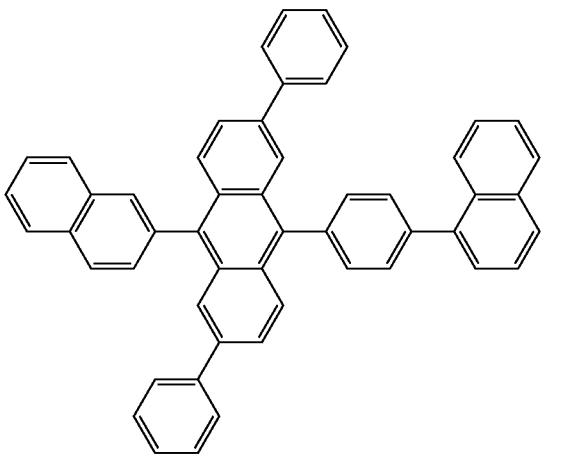

-continued
AN18
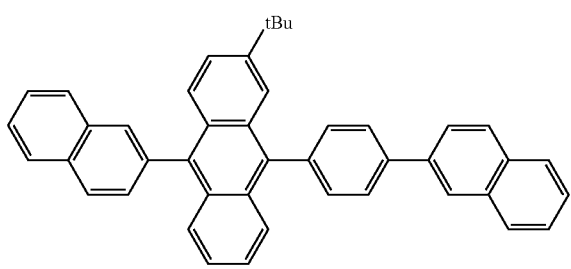
AN19
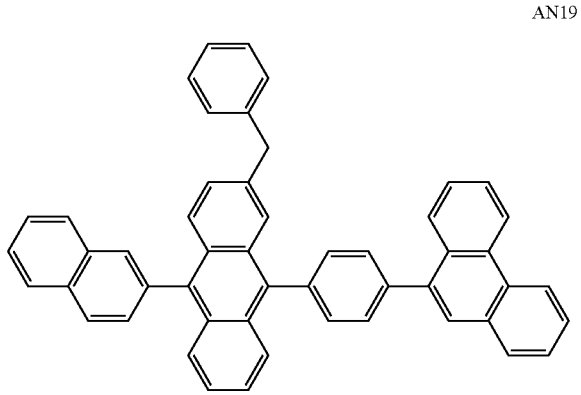
AN20
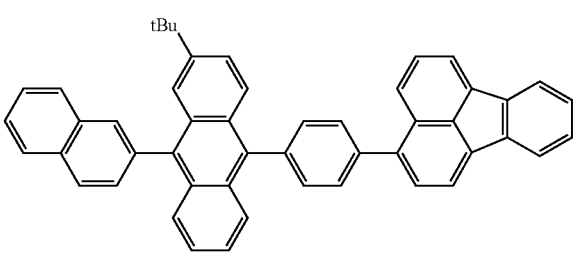
AN21
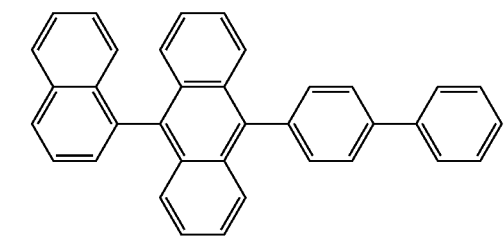
AN22
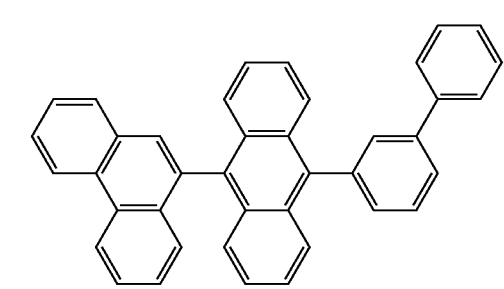
-continued
AN23
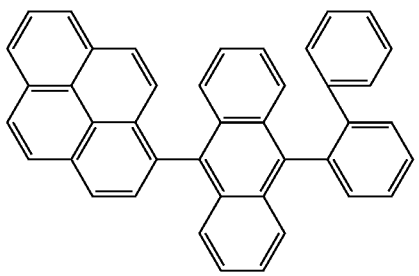
AN24
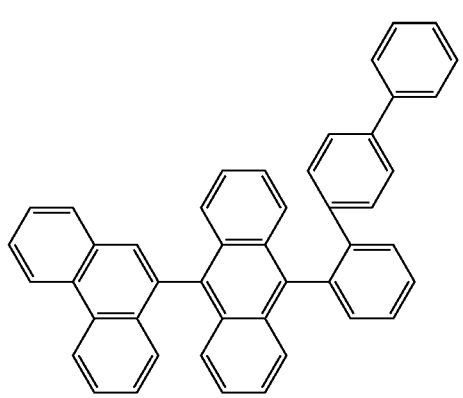
AN25
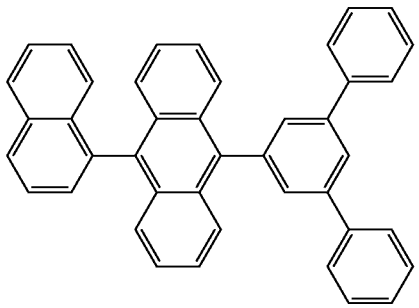
AN26
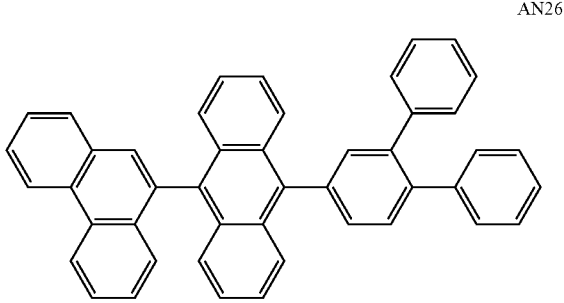
AN27
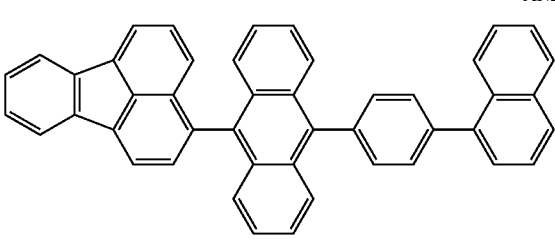

-continued
AN28
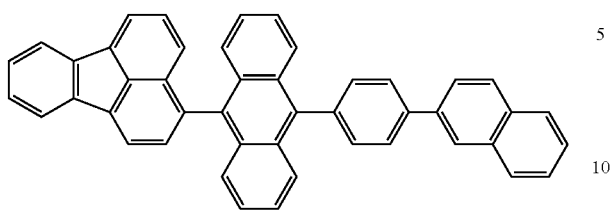
AN29
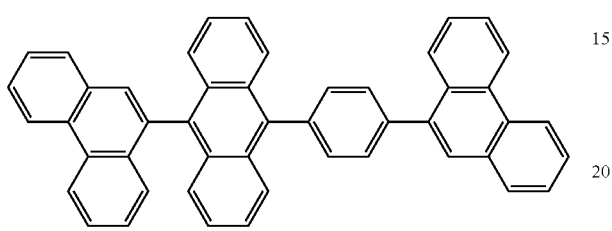
AN30
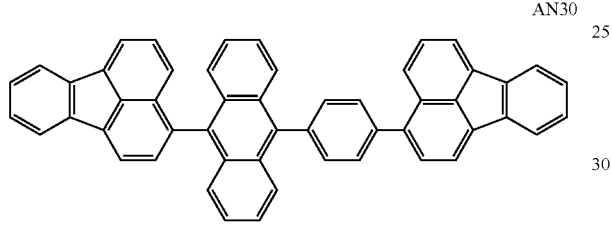
AN31
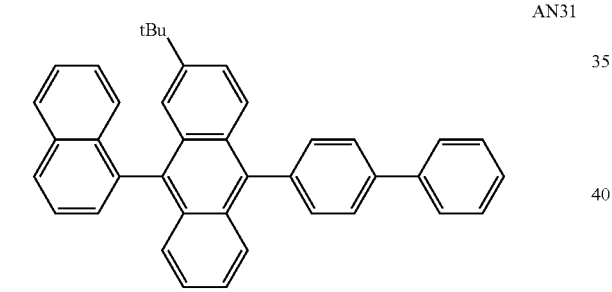
AN32
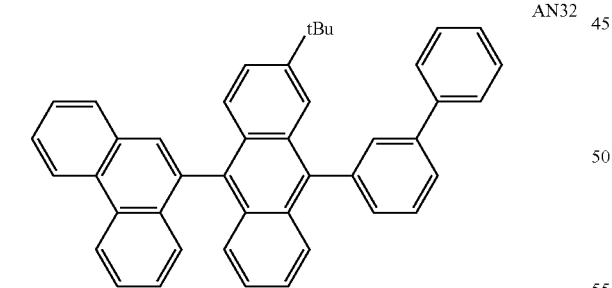
AN33
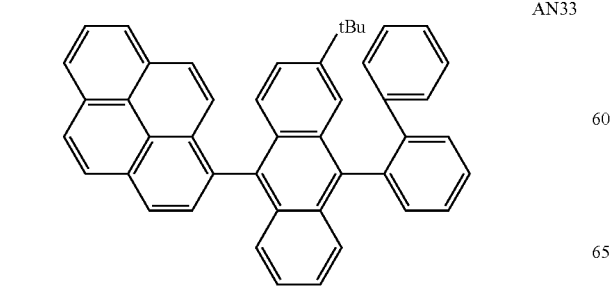
-continued
AN34
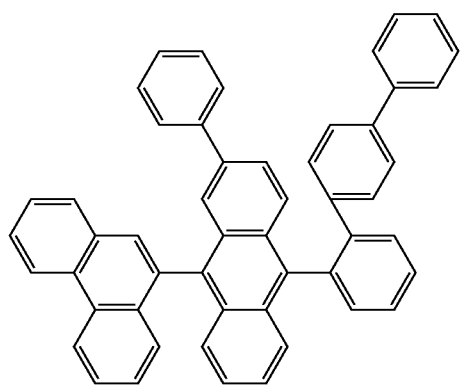
AN35
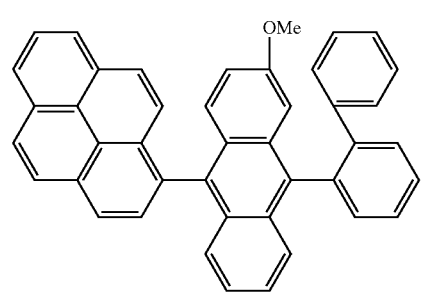
AN36
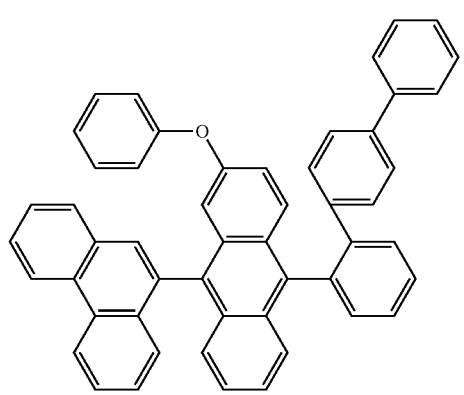
AN37
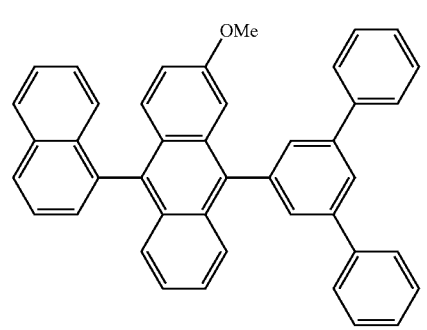

AN38
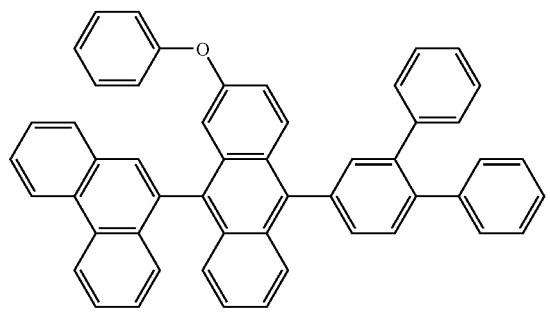
AN39
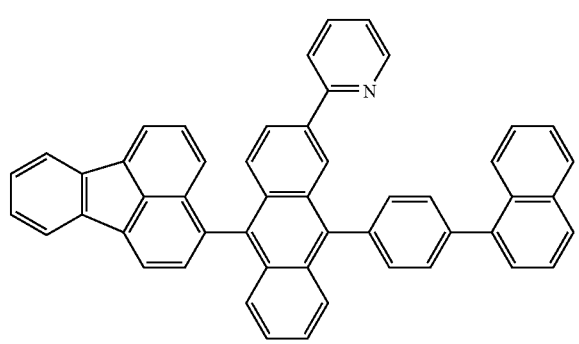
AN43
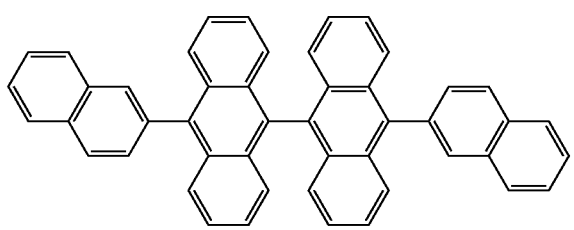
AN40
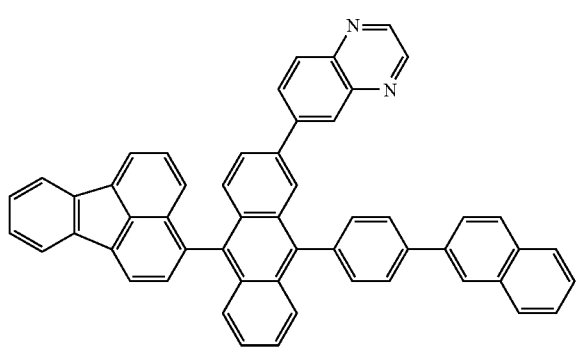
AN41
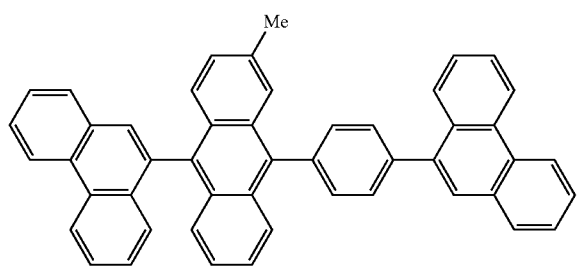
AN42
AN44
AN45
AN46
AN47
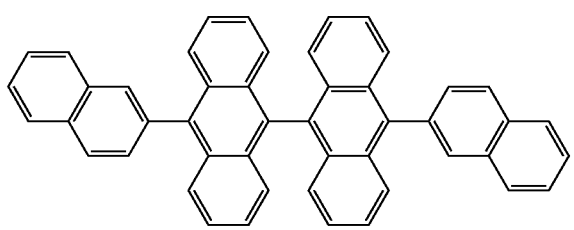

-continued
AN48
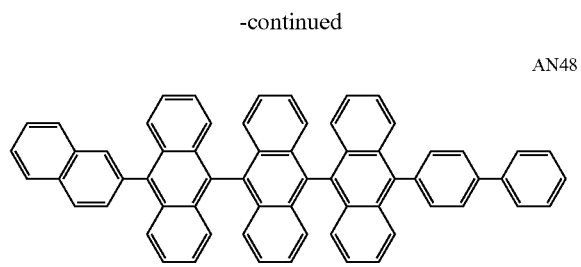
AN49
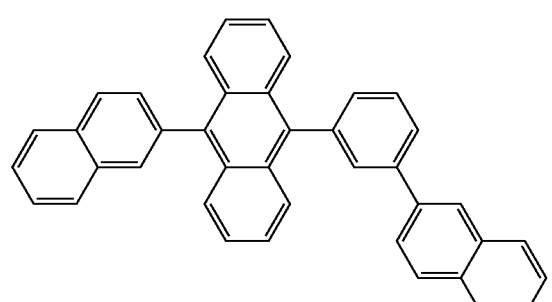
AN50
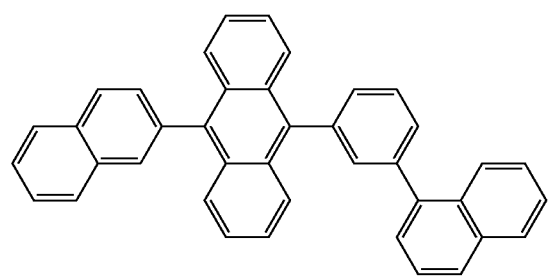
AN51
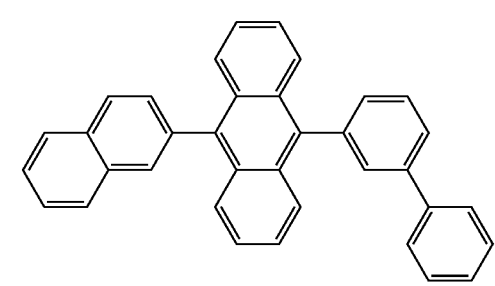
-continued
AN52
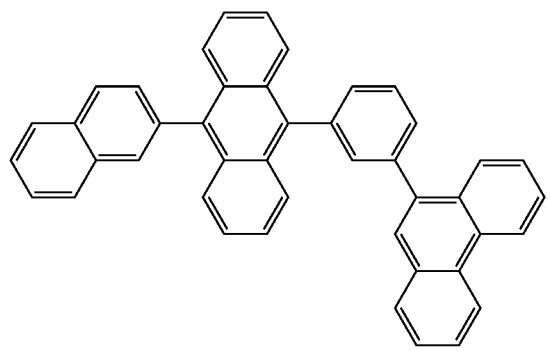
AN53
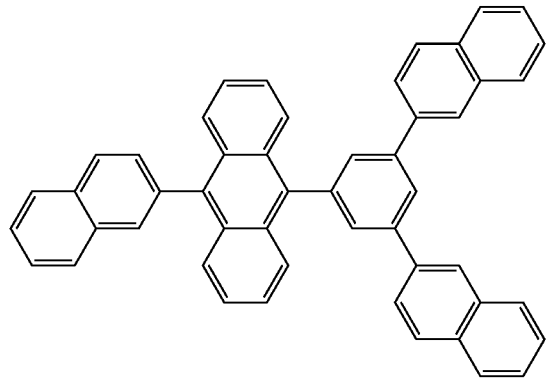
AN54
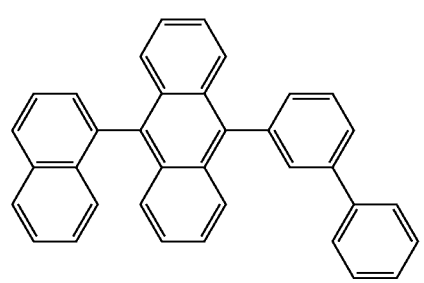
AN55
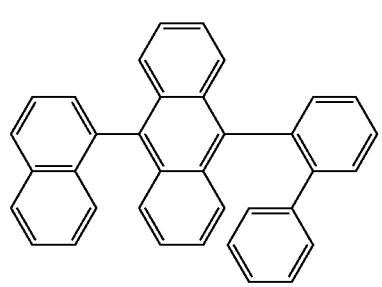

-continued

AN56
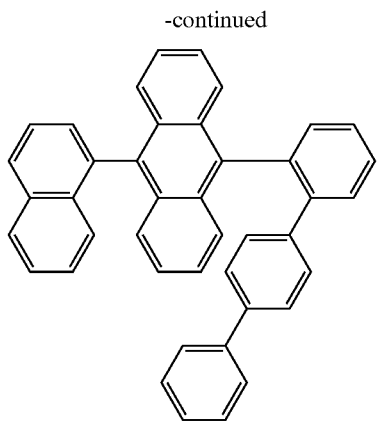

AN57
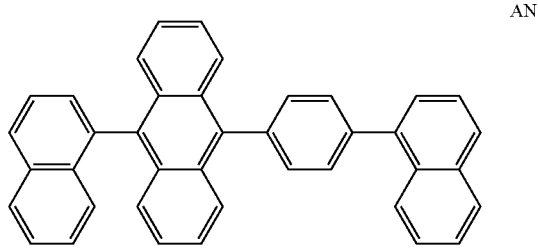

AN58
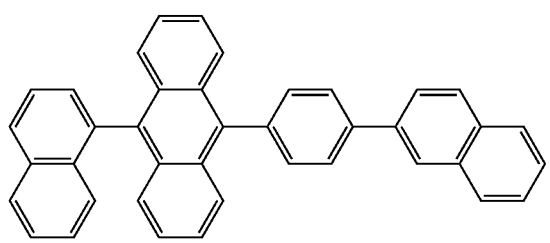

AN59
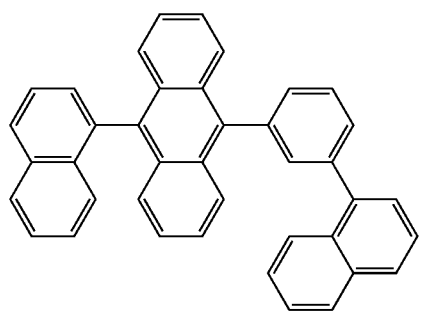

AN60
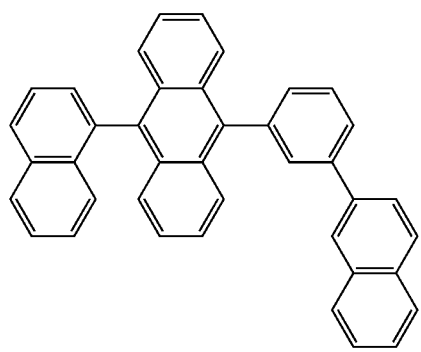

The anthracene derivative represented by general formula (2) of the present invention is a novel compound, which is included in the compound represented by general formula (1).

In general formula (2), Ar represents a substituted or unsubstituted condensed aromatic group having 10 to 50 nuclear carbon atoms.

In general formula (2), Ar' represents a substituted or unsubstituted aromatic group having 6 to 50 nuclear carbon atoms.

In general formula (2), X represents a substituted or unsubstituted aromatic group having 6 to 50 nuclear carbon atoms, a substituted or unsubstituted aromatic heterocyclic group having 5 to 50 nuclear atoms, a substituted or unsubstituted alkyl group having 1 to 50 carbon atoms, a substituted or unsubstituted alkoxyl group having 1 to 50 carbon atoms, a substituted or unsubstituted aralkyl group having 6 to 50 carbon atoms, a substituted or unsubstituted aryloxyl group having 5 to 50 nuclear atoms, a substituted or unsubstituted arylthio group having 5 to 50 nuclear atoms, a substituted or unsubstituted alkoxycarbonyl group having 1 to 50 carbon atoms, carboxyl group, a halogen atom, cyano group, nitro group or hydroxyl group.

Examples of the groups represented by Ar, Ar' and X include the same groups as the groups described as the examples of the corresponding groups in general formula (1).

Examples of the substituent in the groups represented by Ar, Ar' and X include halogen atoms, hydroxyl group, nitro group, cyano group, alkyl groups, aryl groups, cycloalkyl groups, alkoxyl groups, aromatic heterocyclic groups, aralkyl groups, aryloxyl groups, arylthio groups, alkoxycarbonyl groups and carboxyl group.

In general formula (2), a and b each represent an integer of 0 to 4 and preferably 0 or 1.

n represents an integer of 1 to 3 and, when n represents 2 or 3, the plurality of groups represented by the formula shown in [ ] may be the same with or different from each other.

Examples of the anthracene derivative represented by general formula (2) include (AN1) to (AN4), (AN7) to (AN14), (AN17) to (AN24), (AN27) to (AN36), (AN39) to (AN43) and (AN46) to (AN48) among the compounds shown as the examples of the anthracene derivative represented by general formula (1). However, anthracene derivative represented by general formula (2) is not limited to the examples shown above.

It is preferable that the anthracene derivative represented by general formula (2) of the present invention is used as the material for organic EL devices.

The anthracene derivative represented by general formula (1) or (2) of the present invention which is used for organic EL devices can be synthesized in accordance with a suitable combination of the Suzuki coupling reaction, the halogenation reaction and the boration reaction using a halogenated anthracene derivative and a commercial arylboric acid, an arylboric acid synthesized in accordance with a known process or a derivative thereof as the starting materials. The reaction scheme is shown in the following.

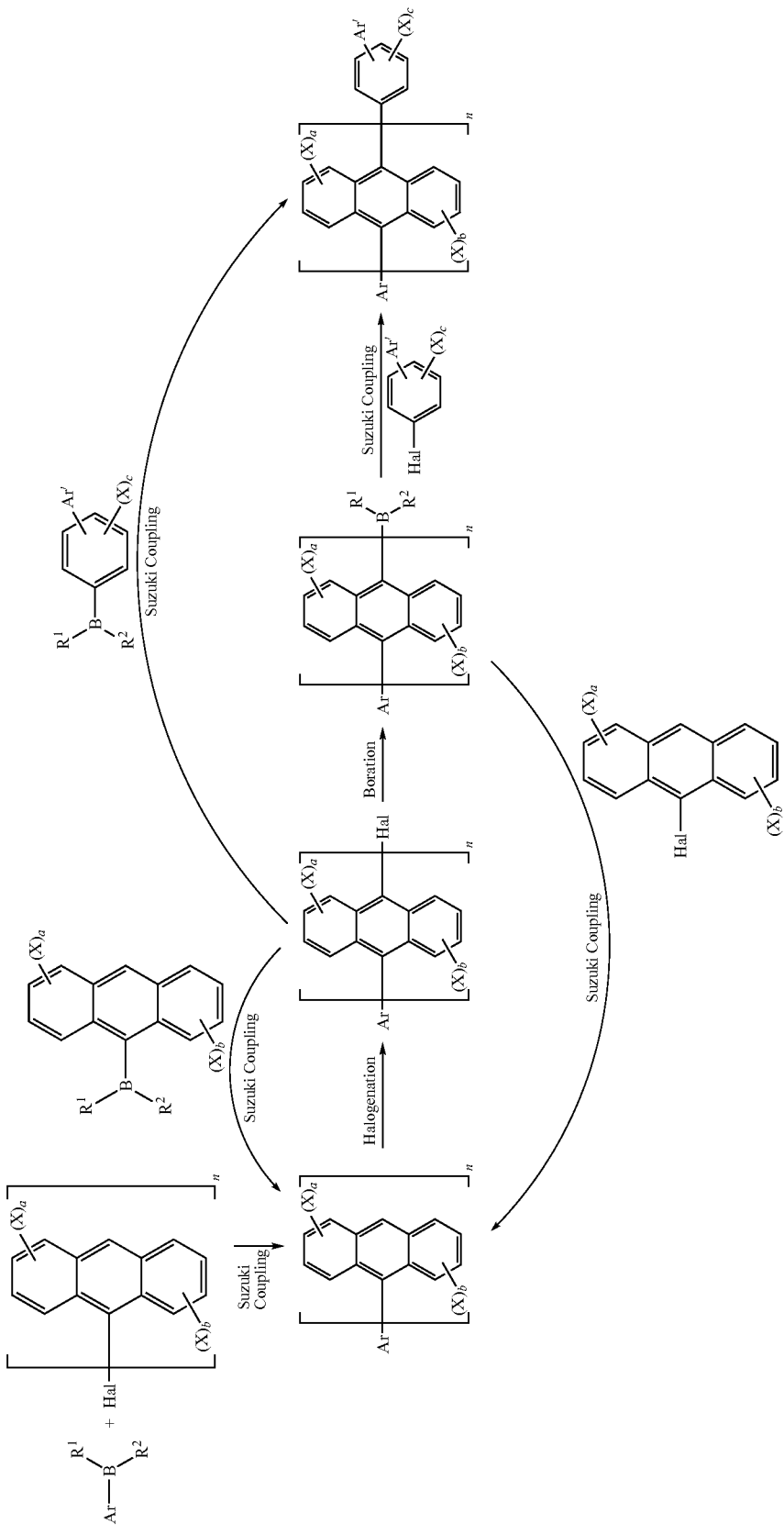
Ar, Ar', X, a-c, n: as defined above.
R[1] and R[2]: hydroxyl goup or alkoxyl group which may have a substituent. R[1] and R[2] may be bonded to form a ring.

Many reports are found on the Suzuki coupling reaction (Chem. Rev. Vol. 95, No. 7, 2475 (1995) and others). The reaction can be conducted under the conditions described in these reports.

The reaction is, in general, conducted under an inert atmosphere such as the atmospheres of nitrogen, argon and helium and may be conducted under a pressurized condition, where necessary. The reaction temperature is in the range of 15 to 300° C. and preferably in the range of 30 to 200° C.

As the solvent for the reaction, water, aromatic hydrocarbons such as benzene, toluene and xylene, ethers such as 1,2-dimethoxyethane, diethyl ether, methyl t-butyl ether, tetrahydrofuran and dioxane; saturated hydrocarbons such as pentane, hexane, heptane, octane and cyclohexane, halides such as dichloromethane, chloroform, carbon tetrachloride, 1,2-dichloroethane and 1,1,1-trichloroethane, nitrites such as acetonitrile and benzonitrile, esters such as ethyl acetate, methyl acetate and butyl acetate, and amides such as N,N-dimethylformamide, N,N-dimethylacetamide and N-methylpyrrolidone, can be used singly or as a mixture. Among these solvents, toluene, 1,2-dimethoxyethane, dioxane and water are preferable. The amount by weight of the solvent is, in general, in the range of 3 to 50 times as much as and preferably in the range of 4 to 20 times as much as the amount by weight of the arylboric acid or the derivative thereof.

Examples of the base used in the reaction include sodium carbonate, potassium carbonate, sodium hydroxide, potassium hydroxide, sodium hydrogencarbonate, potassium hydrogencarbonate, magnesium carbonate, lithium carbonate, potassium fluoride, cesium fluoride, cesium chloride, cesium bromide, cesium carbonate, potassium phosphate, methoxysodium, t-butoxypotassium and t-butoxylithium. Among these bases, sodium carbonate is preferable. The amount of the salt is, in general, in the range of 0.7 to 10 mole equivalents and preferably in the range of 0.9 to 6 mole equivalents based on the amount of the arylboric acid or the derivative thereof.

Examples of the catalyst used in the reaction include palladium catalysts such as tetrakis(triphenylphosphine)palladium, dichlorobis-(triphenylphosphine)palladium, dichloro[bis(diphenylphosphino)ethane]-palladium, dichloro[bis(diphenylphosphino)propane]palladium, dichloro-[bis(diphenylphosphino)butane]palladium and dichloro[bis(diphenyl-phosphino)ferrocene]palladium; and nickel catalysts such as tetrakis-(triphenylphosphine)nickel, dichlorobis(triphenylphosphine)nickel, dichloro[bis(diphenylphosphino)ethane]nickel, dichloro[bis(diphenyl-phosphino)propane]nickel, dichloro[bis(diphenylphosphino)butane]nickel and dichloro[bis(diphenylphosphino)ferrocene]nickel. Among these catalysts, tetrakis(triphenylphosphine)palladium is preferable. The amount of the catalyst is, in general, in the range of 0.001 to 1 mole equivalent and preferable in the range of 0.01 to 0.1 mole equivalent based on the amount of the halogenated anthracene derivative.

Examples of the halogen in the halogenated anthracene derivative include iodine atom, bromine atom and chlorine atom. Iodine atom and bromine atom are preferable.

The halogenating agent in the halogenation reaction is not particularly limited. For example, N-halogenated succinimides are preferable. The amount of the halogenating agent is, in general, in the range of 0.8 to 10 mole equivalents and preferably in the range of 1 to 5 mole equivalents based on the amount of the anthracene derivative.

The reaction is, in general, conducted under an inert atmosphere such the atmospheres of nitrogen, argon and helium in an inert solvent. Examples of the inert solvent include N,N-dimethylformamide, N,N-dimethylacetamide, N-methylpyrrolidone, dimethyl sulfoxide, carbon tetrachloride, chlorobenzene, dichlorobenzene, nitrobenzene, toluene, xylene, methylcellosolve, ethylcellosolve and water. Among these solvents, N,N-dimethylformamide and N-methylpyrrolidone are preferable. The amount by weight of the solvent is, in general, in the range of 3 to 50 time as much as and preferably in the range of 5 to 20 times as much as the amount by weight of the anthracene derivative. The reaction is conducted at a temperature in the range of 0 to 200° C. and preferably in the range of 20 to 120° C.

The boration reaction can be conducted in accordance with a known process (Jikken Kagaku Koza, $4^{th}$ edition, edited by the Chemical Society of Japan, Volume 24, Pages 61 to 90; J. Org. Chem. Vol. 60, 7508 (1995); and others). For example, when the reaction contains the lithiation reaction or the Grignard reaction of a halogenated anthracene derivative, in general, the reaction is conducted under an inert atmosphere such as the atmospheres of nitrogen, argon and helium, and an inert solvent is used as the solvent. As the inert solvent, for example, a saturated hydrocarbon such as pentane, hexane, heptane, octane and cyclohexane, an ether such as 1,2-dimethoxyethane, diethyl ether, methyl t-butyl ether, tetrahydrofuran and dioxane, or an aromatic hydrocarbon such as toluene and xylene, can be used singly or as a mixed solvent. It is preferable that diethyl ether or toluene is used. The amount by weight of the solvent is, in general, in the range of 3 to 50 times as much as and preferably in the range of 4 to 20 times as much as the amount by weight of the halogenated anthracene derivative.

Examples of the lithiating agent include alkyl metal reagents such as n-butyllithium, t-butyllithium, phenyllithium and methyllithium; and amide bases such as lithium diisopropylamide and lithium bistrimethylsilylamide. Among these agents, n-butyllithium is preferable. The Grignard reagent can be prepared by the reaction of the halogenated anthracene derivative and metallic magnesium. As the trialkyl borate of the borating reagent, for example, trimethyl borate, triethyl borate, triisopropyl borate and tributyl borate can be used. Trimethyl borate and triisopropyl borate are preferable.

The amounts of the lithiating agent and the metallic magnesium are each, in general, in the range of 1 to 10 mole equivalents and preferably in the range of 1 to 2 mole equivalents base on the amount of the halogenated anthracene derivative. The amount of the trialkyl borate is, in general, in the range of 1 to 10 mole equivalents and preferably in the range of 1 to 5 mole equivalents based on the amount of the halogenated anthracene derivative. The reaction temperature is, in general, in the range of −100 to 50° C. and preferably in the range of −75 to In the organic EL device of the present invention, it is preferable that the light emitting layer comprises the anthracene derivative represented by general formula (1) or (2) as the main component.

In the organic EL device of the present invention, it is preferable that the light emitting layer further comprises an arylamine compound and/or a styrylamine compound.

As the styrylamine compound, compounds represented by the following general formula (A):

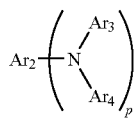

wherein $Ar_2$ represent a group selected from phenyl group, biphenyl group, terphenyl group, stilbene group and distyrylaryl groups, $Ar_3$ and $Ar_4$ each represent hydrogen atom or an aromatic group having 6 to 20 carbon atoms, the groups represented by $Ar_2$, $Ar_3$ and $Ar_4$ may be substituted, p represents an integer of 1 to 4 and, preferably, at least one of the groups represented by $Ar_3$ and $Ar_4$ is substituted with styryl group, are preferable.

Examples of the aromatic group having 6 to 20 carbon atoms include phenyl group, naphthyl group, anthranyl group, phenanthryl group and terphenyl group.

As the arylamine compound, compounds represented by the following general formula (B):

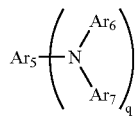

wherein $Ar_5$ to $Ar_7$ each represent an aryl group having 5 to 40 nuclear carbon atoms, and q represents an integer of 1 to 4, are preferable.

Examples of the aryl group having 5 to 40 nuclear carbon atoms include phenyl group, naphthyl group, anthranyl group, phenanthryl group, pyrenyl group, coronyl group, biphenyl group, terphenyl group, pyrrolyl group, furanyl group, thiophenyl group, benzothiophenyl group, oxadiazolyl group, diphenylanthranyl group, indolyl group, carbazolyl group, pyridyl group, benzoquinolyl group, fluoranthenyl group, acenaphthofluoranthenyl group and stilbene group. Preferable examples of the substituent to the aryl group include alkyl groups having 1 to 6 carbon atoms such as ethyl group, methyl group, i-propyl group, n-propyl group, s-butyl group, t-butyl group, pentyl group, hexyl group, cyclopentyl group and cyclohexyl group; alkoxyl groups having 1 to 6 carbon atoms such as ethoxyl group, methoxyl group, i-propoxyl group, n-propoxyl group, s-butoxyl group, t-butoxyl group, pentoxyl group, hexyloxyl group, cyclopentoxyl group and cyclohexyloxyl group; aryl groups having 5 to 40 nuclear atoms; amino groups substituted with an aryl group having 5 to 40 nuclear atoms; ester groups having an aryl group having 5 to 40 nuclear atoms; ester groups having an alkyl group having 1 to 6 carbon atoms; cyano group; nitro group; and halogen atoms.

The construction of the device in the organic EL device of the present invention will be described in the following.

Typical examples of the construction of the organic EL device include:

(1) An anode/a light emitting layer/a cathode;

(2) An anode/a hole injecting layer/a light emitting layer/a cathode;

(3) An anode/a light emitting layer/an electron injecting layer/a cathode;

(4) An anode/a hole injecting layer/a light emitting layer/an electron injecting layer/a cathode;

(5) An anode/an organic semiconductor layer/a light emitting layer/a cathode;

(6) An anode/an organic semiconductor layer/an electron barrier layer/a light emitting layer/a cathode;

(7) An anode/an organic semiconductor layer/a light emitting layer/an adhesion improving layer/a cathode;

(8) An anode/a hole injecting layer/a hole transporting layer/a light emitting layer/an electron injecting layer/a cathode;

(9) An anode/an insulating layer/a light emitting layer/an insulating layer/a cathode;

(10) An anode/an inorganic semiconductor layer/an insulating layer/a light emitting layer/an insulating layer/a cathode;

(11) An anode/an organic semiconductor layer/an insulating layer/a light emitting layer/an insulating layer/a cathode;

(12) An anode/an insulating layer/a hole injecting layer/a hole transporting layer/a light emitting layer/an insulating layer/a cathode; and

(13) An anode/an insulating layer/a hole injecting layer/a hole transporting layer/a light emitting layer/an electron injecting layer/a cathode.

Among the above constructions, construction (8) is preferable. However, the construction of the organic EL device is not limited to those shown above as the examples.

In general, the organic EL device is prepared on a substrate which transmits light. The substrate which transmits light is the substrate which supports the organic EL device. It is preferable that the substrate which transmits light has a transmittance of light of 50% or greater in the visible region of 400 to 700 nm. It is also preferable that a flat and smooth substrate is used.

As the substrate which transmits light, for example, glass plates and synthetic resin plates are advantageously used. Examples of the glass plate include plates made of soda lime glass, glass containing barium and strontium, lead glass, aluminosilicate glass, borosilicate glass, barium borosilicate glass and quartz. Examples of the synthetic resin plate include plates made of polycarbonate resins, acrylic resins, polyethylene terephthalate resins, polyether sulfide resins and polysulfone resins.

As the anode, an electrode made of a material such as a metal, an alloy, a conductive compound and a mixture of these materials which has a great work function (4 eV or more) is preferable. Specific examples of the material for the anode include metals such as Au and conductive materials such as CuI, ITO (indium tin oxide), $SnO_2$, ZnO and In—Zn—O. The anode can be prepared by forming a thin film of the electrode material described above in accordance with a process such as the vapor deposition process and the sputtering process. When the light emitted from the light emitting layer is obtained through the anode, it is preferable that the anode has a transmittance of the emitted light greater than 10%. It is also preferable that the sheet resistivity of the anode is several hundred $\Omega/\square$ or smaller. The thickness of the anode is, in general, selected in the range of 10 nm to 1 μm and preferably in the range of 10 to 200 nm.

In the organic EL device of the present invention, it is preferable that a layer of a chalcogenide, a metal halide or a metal oxide (this layer may occasionally be referred to as a surface layer) is disposed on the surface of at least one of the pair of electrodes prepared as described above. Specifically, it is preferable that a layer of a chalcogenide (including an oxide) of a metal such as silicon and aluminum is disposed on the surface of the anode at the side of the light emitting layer, and a layer of a metal halide or a metal oxide is disposed on the surface of the cathode at the side of the light emitting layer. Due to the above layers, stability in driving can be improved.

Preferable examples of the chalcogenide include $SiO_x$ ($1 \leq x \leq 2$), $AlO_x$ ($1 \leq x \leq 1.5$), SiON and SiAlON. Preferable examples of the metal halide include LiF, $MgF_2$, $CaF_2$ and fluorides of rare earth metals. Preferable examples of the metal oxide include $Cs_2O$, $Li_2O$, MgO, SrO, BaO and CaO.

In the organic EL device of the present invention, it is preferable that a mixed region of an electron transfer compound and a reducing dopant or a mixed region of a hole transfer compound and an oxidizing dopant is disposed on the surface of at least one of the pair of electrodes prepared as described above. Due to the mixed region disposed as described above, the electron transfer compound is reduced to form an anion, and injection and transportation of electrons from the mixed region into the light emitting medium can be facilitated. The hole transfer compound is oxidized to form a cation, and injection and transportation of holes from the mixed region into the light emitting medium is facilitated. Preferable examples of the oxidizing dopant include various types of Lewis acid and acceptor compounds. Preferable examples of the reducing dopant include alkali metals, compounds of alkali metals, alkaline earth metals, rare earth metals and compounds of these metals.

In the organic EL device of the present invention, the light emitting layer has the following functions:

(1) The injecting function: the function of injecting holes from the anode or the hole injecting layer and injecting electrons from the cathode or the electron injecting layer when an electric field is applied;

(2) The transporting function: the function of transporting injected charges (electrons and holes) by the force of the electric field; and (3) The light emitting function: the function of providing the field for recombination of electrons and holes and leading the recombination to the emission of light.

As the process for forming the light emitting layer, a conventional process such as the vapor deposition process, the spin coating process and the LB process can be used. It is particularly preferable that the light emitting layer is a molecular deposit film. The molecular deposit film is a thin film formed by deposition of a material compound in the gas phase or a thin film formed by solidification of a material compound in a solution or in the liquid phase. In general, the molecular deposit film can be distinguished from the thin film formed in accordance with the LB process (the molecular accumulation film) based on the differences in the aggregation structure and higher order structures and functional differences caused by these structural differences.

As disclosed in Japanese Patent Application Laid-Open No. Showa 57(1982)-51781, the light emitting layer can also be formed by dissolving a binder such as a resin and the material compounds into a solvent to prepare a solution, followed by forming a thin film from the prepared solution in accordance with the spin coating process or the like.

In the present invention, where desired, the light emitting layer may comprise conventional light emitting materials other than the light emitting material of the present invention, or a light emitting layer comprising other conventional light emitting material may be laminated to the light emitting layer comprising the light emitting material of the present invention as long as the object of the present invention is not adversely affected.

The hole injecting layer and the hole transporting layer are layers which help injection of holes into the light emitting layer and transport the holes to the light emitting region. The layers exhibit a great mobility of holes and, in general, have an ionization energy as small as 5.5 eV or smaller. For the hole injecting layer and the hole transporting layer, a material which transports holes to the light emitting layer at a small strength of the electric field is preferable. A material which exhibits, for example, a mobility of holes of at least $10^{-6}$ $cm^2$/V·sec under application of an electric field of $10^4$ to $10^6$ V/cm is preferable. A material can be selected as desired from materials which are conventionally used as the charge transporting material of holes in photoconductive materials and conventional materials which are used for the hole injecting layer in organic EL devices.

To form the hole injecting layer or the hole transporting layer, a thin film may be formed from the material for the hole injecting layer or the hole transporting layer, respectively, in accordance with a conventional process such as the vacuum vapor deposition process, the spin coating process, the casting process and the LB process. The thickness of the hole injecting layer and the hole transporting layer is not particularly limited. In general, the thickness is 5 nm to 5 µm.

The electron injection layer and the electron transporting layer are layers which help injection of electrons into the light emitting layer, transport electrons to the light emitting region and exhibit a great mobility of electrons. The adhesion improving layer is a layer made of a material exhibiting excellent adhesion with the cathode among the electron injecting layers. As the material for the electron injecting layer, metal complexes of 8-hydroxyquinoline and derivatives thereof are preferable. Examples of the metal complex of 8-hydroxyquinoline and derivatives thereof include metal chelates of oxinoid compounds including chelates of oxine (in general, 8-quinolinol or 8-hydroxyquinoline). For example, tris(8-quinolinol)aluminum can be used as the electron injecting material.

In general, an organic EL device tends to form defects in pixels due to leak and short circuit since an electric field is applied to ultra-thin films. To prevent the formation of the defects, a layer of an insulating thin film may be inserted between the pair of electrodes.

Examples of the material used for the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide and vanadium oxide. Mixtures and laminates of the above compounds can also be used.

To prepare the organic EL device of the present invention, for example, the anode, the light emitting layer and, where necessary, the hole injecting layer and the electron injecting layer are formed in accordance with the above processes using the above materials, and the cathode is formed in the last step. The organic EL device may be prepared by forming the above layers in the order reverse to that described above, i.e., the cathode being formed in the first step and the anode in the last step.

An embodiment of the process for preparing an organic EL device having a construction in which an anode, a hole injecting layer, a light emitting layer, an electron injecting layer and a cathode are disposed successively on a substrate transmitting light will be described in the following.

On a suitable substrate transmitting light, a thin film made of a material for the anode is formed in accordance with the vapor deposition process or the sputtering process so that the thickness of the formed thin film is 1 μm or smaller and preferably in the range of 10 to 200 nm. The formed thin film is used as the anode. Then, a hole injecting layer is formed on the anode. The hole injecting layer can be formed in accordance with the vacuum vapor deposition process, the spin coating process, the casting process or the LB process, as described above. The vacuum vapor deposition process is preferable since a uniform film can be easily obtained and the possibility of formation of pin holes is small. When the hole injecting layer is formed in accordance with the vacuum vapor deposition process, in general, it is preferable that the conditions are suitably selected in the following ranges: the temperature of the source of the deposition: 50 to 450° C.; the vacuum: $10^{-7}$ to $10^{-3}$ Torr; the rate of deposition: 0.01 to 50 nm/second; the temperature of the substrate: −50 to 300° C. and the thickness of the film: 5 nm to 5 μm; although the conditions of the vacuum vapor deposition are different depending on the used compound (the material for the hole injecting layer) and the crystal structure and the recombination structure of the hole injecting layer to be formed.

Then, the light emitting layer is formed on the hole injecting layer formed above. Using the light emitting material described in the present invention, a thin film of the light emitting material can be formed in accordance with the vacuum vapor deposition process, the sputtering process, the spin coating process or the casting process, and the formed thin film is used as the light emitting layer. The vacuum vapor deposition process is preferable because a uniform film can be easily obtained and the possibility of formation of pin holes is small. When the light emitting layer is formed in accordance with the vacuum vapor deposition process, in general, the conditions of the vacuum vapor deposition process can be selected in the same ranges as those described for the vacuum vapor deposition of the hole injecting layer although the conditions are different depending on the used compound. It is preferable that the thickness is in the range of 10 to 40 nm.

An electron injecting layer is formed on the light emitting layer formed above. Similarly to the hole injecting layer and the light emitting layer, it is preferable that the electron injecting layer is formed in accordance with the vacuum vapor deposition process since a uniform film must be obtained. The conditions of the vacuum vapor deposition can be selected in the same ranges as those described for the vacuum vapor deposition of the hole injecting layer and the light emitting layer.

A cathode is formed on the electron injecting layer formed above in the last step, and an organic EL device can be obtained. The cathode is made of a metal and can be formed in accordance with the vacuum vapor deposition process or the sputtering process. It is preferable that the vacuum vapor deposition process is used in order to prevent formation of damages on the lower organic layers during the formation of the film.

In the above preparation of the organic EL device, it is preferable that the above layers from the anode to the cathode are formed successively while the preparation system is kept in a vacuum after being evacuated.

The organic EL device which can be prepared as described above emits light when a direct voltage of 3 to 40 V is applied in the condition that the anode is connected to a positive electrode (+) and the cathode is connected to a negative electrode (−). When the connection is reversed, no electric current is observed and no light is emitted at all. When an alternating voltage is applied to the organic EL device, the uniform light emission is observed only in the condition that the polarity of the anode is positive and the polarity of the cathode is negative. When an alternating voltage is applied to the organic EL device, any type of wave shape can be used.

The present invention will be described more specifically with reference to examples in the following. However, the present invention is not limited to the examples.

Example 1

Synthesis of 10-(2-naphthyl)anthracene-9-boric acid

Under the atmosphere of argon, a solution prepared by dissolving 549 g of 2-naphthaleneboric acid (manufactured by TOKYO KASEI Co., Ltd.), 684 g of 9-bromoanthracene (manufactured by TOKYO KASEI Co., Ltd.), 61.5 g of tetrakis(triphenylphosphine)palladium(0) (manufactured by TOKYO KASEI Co., Ltd.), 4.9 liters of toluene (manufactured by HIROSHIMA WAKO Co., Ltd.) and 845.9 g of sodium carbonate (manufactured by HIROSHIMA WAKO Co., Ltd.) into 4.9 liters of water was placed into a 20 liter flask, and the resultant mixture was stirred for 24 hours while being heated under the refluxing condition. After the reaction was completed, the reaction mixture was cooled to the room temperature, and formed crystals were separated by filtration. The obtained crystals were recrystallized from toluene, and 751 g of crystals were obtained Under the atmosphere of argon, 750 g of the crystals obtained above and 10 liters of dehydrated dimethylformamide (DMF) (manufactured by HIROSHIMA WAKO Co., Ltd.) were placed into a 20 liter flask, and the resultant mixture was heated at 80° C. After the material was dissolved, 482.4 g of N-bromosuccinimide (manufactured by HIROSHIMA WAKO Co., Ltd.) was added at 50° C., and the resultant mixture was stirred for 2 hours. After the reaction was completed, the reaction solution was poured into 20 liters of purified water, and formed crystals were separated by filtration. The separated crystals were recrystallized from toluene, and 689 g of crystals were obtained.

Under the atmosphere of argon, 588 g of the crystals obtained above, 4.5 liters of dehydrated ether (manufactured by HIROSHIMA WAKO Co., Ltd.) and 4.5 liters of dehydrated toluene (manufactured by HIROSHIMA WAKO Co., Ltd.) were placed into a 20 liter flask, and the resultant mixture was cooled at −64° C. in a dry ice bath. To the cooled mixture, 1.2 liters of a 1.6 M hexane solution of butyllithium (manufactured by HIROSHIMA WAKO Co., Ltd.) was added dropwise over 30 minutes, and the reaction was allowed to proceed at −64° C. for 2 hours. To the resultant reaction mixture, 866 g of triisopropyl borate (manufactured by TOKYO KASEI Co., Ltd.) was added dropwise over 20 minutes. After the addition was completed, the temperature was adjusted at the room temperature, and the reaction mixture was stirred for 12 hours. After the resultant reaction mixture was cooled with ice, 4 liters of 2 N hydrochloric acid was added at a temperature of 10° C. or lower, and 1 liter of toluene was added. The organic phase separated from the resultant mixture was dried with sodium sulfate and concentrated under a reduced pressure. Hexane was added to the resultant solution, and formed crystals were separated by filtration. The obtained crystals were dissolved into 5 liters of tetrahydrofuran. To the resultant solution, 500 ml of concentrated hydrochloric acid and 5 g of tetrabutylammonium bromide were added, and the resultant mixture was stirred for 12 hours. The formed crystals were separated by filtration and dried, and 431 g of crystals were obtained.

Since m/z=348 in the field desorption mass analysis (FD-MS) of the obtained compound, which corresponded to $C_{24}H_{17}BO_2$=348, the compound was identified to be 10-(2-naphthyl)anthracene-9-boric acid (the yield: 47%).

Synthesis Example 2

Synthesis of 2-(4-bromophenyl)naphthalene

Under the atmosphere of argon, a solution prepared by dissolving 7.1 g of 2-naphthaleneboric acid (manufactured by TOKYO KASEI Co., Ltd.), 12.9 g of 4-iodobromobenzene (manufactured by TOKYO KASEI Co., Ltd.), 0.6 g of tetrakis (triphenylphosphine)palladium(0) (manufactured by TOKYO KASEI Co., Ltd.) and 12.7 g of sodium carbonate (manufactured by HIROSHIMA WAKO Co., Ltd.) into 60 ml of water was placed into a 300 ml flask, and the resultant mixture was stirred for 24 hours while being heated under the refluxing condition. After the reaction was completed, the reaction mixture was cooled to the room temperature, and formed crystals were separated by filtration. The obtained crystals were recrystallized from toluene, and 9.0 g of crystals were obtained Since m/z=284 in FD-MS of the obtained compound, which corresponded to $C_{16}H_{11}Br$=283, the compound was identified to be 2-(4-bromophenyl)naphthalene (the yield: 77%).

Synthesis Example 3

Synthesis of 3-(4-bromophenyl)fluoranthene

Under the atmosphere of argon, 62 g of fluoranthene and 250 ml of dehydrated DMF (manufactured by HIROSHIMA WAKO Co., Ltd.) were placed into a 500 ml flask and heated at 80° C. After the material was dissolved, 60 g of N-bromosuccinimide (manufactured by HIROSHIMA WAKO Co., Ltd.) was added at 50° C., and the resultant mixture was stirred for 2 hours. After the reaction was completed, the reaction solution was poured into 500 ml of purified water, and formed crystals were separated by filtration. The separated crystals were purified in accordance with the column chromatography, and 10.5 g of crystals were obtained.

Under the atmosphere of argon, 10.0 g of the crystals obtained above, 120 ml of dehydrated ether (manufactured by HIROSHIMA WAKO Co., Ltd.) and 120 ml of dehydrated toluene (manufactured by HIROSHIMA WAKO Co., Ltd.) were placed into a 500 ml flask, and the resultant mixture was cooled at −0.64° C. in a dry ice bath. To the cooled mixture, 25 ml of a 1.6 M hexane solution of butyllithium (manufactured by HIROSHIMA WAKO Co., Ltd.) was added dropwise over 30 minutes, and the reaction was allowed to proceed at −64° C. for 2 hours. To the resultant reaction mixture, 8 g of triisopropyl borate (manufactured by TOKYO KASEI Co., Ltd.) was added dropwise over 20 minutes. After the addition was completed, the temperature was adjusted at the room temperature, and the reaction mixture was stirred for 12 hours. After the resultant reaction mixture was cooled with ice, 100 ml of 2 N hydrochloric acid was added at a temperature of 10° C. or lower, and 25 ml of toluene was added. The organic phase separated from the resultant mixture was dried with sodium sulfate and concentrated under a reduced pressure. Hexane was added to the resultant solution, and formed crystals were separated by filtration. The obtained crystals were dissolved into 120 ml of tetrahydrofuran. To the resultant solution, 15 ml of concentrated hydrochloric acid and 0.15 g of tetrabutylammonium bromide were added, and the resultant mixture was stirred for 12 hours. The formed crystals were separated by filtration and dried, and 7.0 g of crystals of 3-fluorantheneboric acid were obtained.

Under the atmosphere of argon, a solution prepared by dissolving 7.0 g of the crystals obtained above (manufactured by TOKYO KASEI Co., Ltd.), 9.0 of 4-iodobromobenzene (manufactured by TOKYO KASEI Co., Ltd.), 0.6 g of tetrakis (triphenylphosphine)palladium(0) (manufactured by TOKYO KASEI Co., Ltd.) and 12.7 g of sodium carbonate (manufactured by HIROSHIMA WAKO Co., Ltd.) into 60 ml of water was placed into a 300 ml flask, and the resultant mixture was stirred for 24 hours while being heated under the refluxing condition. After the reaction was completed, the reaction mixture was cooled to the room temperature, and formed crystals were separated by filtration. The obtained crystals were recrystallized from toluene, and 6.4 g of crystals were obtained Since m/z=358 and 356 in FD-MS of the obtained compound, which corresponded to $C_{22}H_{15}Br$=357, the compound was identified to be 3-(4-bromophenyl)fluoranthene (the yield: 6%).

Synthesis Example 4

Synthesis of 10-(3-fluoranthenyl)anthracene-9-boric acid

Under the atmosphere of argon, a solution prepared by dissolving 7.85 g of 3-fluorantheneboric acid, 6.84 g of 9-bromoanthracene (manufactured by TOKYO KASEI Co., Ltd.), 0.6 g of tetrakis-(triphenylphosphine)palladium(0) (manufactured by TOKYO KASEI Co., Ltd.), 50 ml of toluene (manufactured by HIROSHIMA WAKO Co., Ltd.) and 8.5 g of sodium carbonate (manufactured by HIROSHIMA WAKO Co., Ltd.) into 50 ml of water was placed into a 300 ml flask, and the resultant mixture was stirred for 24 hours while being heated under the refluxing condition. After the reaction was completed, the reaction mixture was cooled to the room temperature, and formed crystals were separated by filtration. The obtained crystals were recrystallized from toluene, and 4.6 g of crystals were obtained Under the atmosphere of argon, 4.5 g of the crystals obtained above and 100 ml of dehydrated DMF (manufactured by HIROSHIMA WAKO Co., Ltd.) were placed into a 300 ml flask, and the resultant mixture was heated at 80° C. After the material was dissolved, 2.3 g of N-bromosuccinimide (manufactured by HIROSHIMA WAKO Co., Ltd.) was added at 50° C., and the resultant mixture was stirred for 2 hours. After the reaction was completed, the reaction solution was poured into 200 ml of purified water, and formed crystals were separated by filtration. The separated crystals were recrystallized from toluene, and 4.5 g of crystals were obtained.

Under the atmosphere of argon, 4.5 g of the crystals obtained above, 50 ml of dehydrated ether (manufactured by HIROSHIMA WAKO Co., Ltd.) and 50 ml of dehydrated toluene (manufactured by HIROSHIMA WAKO Co., Ltd.) were placed into a 300 ml flask, and the resultant mixture was cooled at −64° C. in a dry ice bath. To the cooled mixture, 7 ml of a 1.6 M hexane solution of butyllithium (manufactured by HIROSHIMA WAKO Co., Ltd.) was added dropwise over 30 minutes, and the reaction was allowed to proceed at −64° C. for 2 hours. To the resultant reaction mixture, 5.6 g of triisopropyl borate (manufactured by TOKYO KASEI Co., Ltd.) was added dropwise over 20 minutes. After the addition was completed, the temperature was adjusted at the room temperature, and the reaction mixture was stirred for 12 hours.

After the resultant reaction mixture was cooled with ice, 40 ml of 2 N hydrochloric acid was added at a temperature of 10° C. or lower, and 10 ml of toluene was added. The organic phase separated from the resultant mixture was dried with sodium sulfate and concentrated under a reduced pressure. Hexane was added to the resultant solution, and formed crystals were separated by filtration. The obtained crystals were dissolved into 50 ml of tetrahydrofuran. To the resultant solution, 5 ml of concentrated hydrochloric acid and 0.1 g of tetrabutylammonium bromide were added, and the resultant mixture was stirred for 12 hours. The formed crystals were separated by filtration and dried, and 3.6 g of crystals were obtained.

Since m/z=422 in FD-MS of the obtained compound, which corresponded to $C_{30}H_{19}BO_2$=422, the compound was identified to be 10-(3-fluoranthenyl)anthracene-9-boric acid (the yield: 32%).

Synthesis Example 5

Synthesis of 1-(4-bromophenyl)naphthalene

The same procedures as those conducted in Synthesis Example 2 were conducted except that 1-naphthaleneboric acid was used in place of 2-naphthaleneboric acid, and 29.9 g of a colorless oily substance was obtained.

Since m/z=284 and 282 in FD-MS of the obtained compound, which corresponded to $C_{16}H_{11}Br$=283, the compound was identified to be 1-(4-bromophenyl)naphthalene (the yield: 88%).

Synthesis Example 6

Synthesis of 2-(3-bromophenyl)naphthalene

The same procedures as those conducted in Synthesis Example 2 were conducted except that 3-iodobromobenzene was used in place of 4-iodobromobenzene, and 20.1 g of a colorless oily substance was obtained.

Since m/z=284 and 282 in FD-MS of the obtained compound, which corresponded to $C_{16}H_{11}Br$=283, the compound was identified to be 2-(3-bromophenyl)naphthalene (the yield: 75%).

Example 1

Synthesis of a compound (AN8)

Under the atmosphere of argon, a solution prepared by dissolving 5.98 g of 10-(2-naphthyl)anthracene-9-boric acid obtained in Synthesis Example 1, 4.05 g of 2-(4-bromophenyl)naphthalene obtained in Synthesis Example 2, 0.33 g of tetrakis(triphenylphosphine)palladium(0) (manufactured by TOKYO KASEI Co., Ltd.), 60 ml of 1,2-dimethoxyethane (manufactured by HIROSHIMA WAKO Co., Ltd.) and 4.55 g of sodium carbonate (manufactured by HIROSHIMA WAKO Co., Ltd.) into 21 ml of water was placed into a 300 ml flask, and the resultant mixture was stirred for 24 hours while being heated under the refluxing condition. After the reaction was completed, the reaction mixture was cooled to the room temperature, and formed crystals were separated by filtration. The obtained compound was purified in accordance with the column chromatography, and 3.4 g of a light yellow solid substance was obtained Since m/z=506 in FD-MS of the obtained compound, which corresponded to $C_{40}H_{26}$=506, the compound was identified to be AN8 (the yield: 47%).

Example 2

Synthesis of a Compound (AN10)

Under the atmosphere of argon, a solution prepared by dissolving 5.98 g of 10-(2-naphthyl)anthracene-9-boric acid obtained in Synthesis Example 1, 5.13 g of 3-(4-bromophenyl)fluoranthene obtained in Synthesis Example 3, 0.33 g of tetrakis(triphenylphosphine)palladium(0) (manufactured by TOKYO KASEI Co., Ltd.), 60 ml of 1,2-dimethoxyethane (manufactured by HIROSHIMA WAKO Co., Ltd.) and 4.55 g of sodium carbonate (manufactured by HIROSHIMA WAKO Co., Ltd.) into 21 ml of water was placed into a 300 ml flask, and the resultant mixture was stirred for 24 hours while being heated under the refluxing condition. After the reaction was completed, the reaction mixture was cooled to the room temperature, and formed crystals were separated by filtration. The obtained compound were purified in accordance with the column chromatography, and 3.3 g of a light yellow solid substance was obtained Since m/z=580 in FD-MS of the obtained compound, which corresponded to $C_{46}H_{28}$=580, the compound was identified to be AN10 (the yield: 40%).

Example 3

Synthesis of a Compound (AN28)

Under the atmosphere of argon, a solution prepared by dissolving 7.24 g of 10-(3-fluoranthenyl)anthracene-9-boric acid obtained in Synthesis Example 4, 4.05 g of 2-(4-bromophenyl)naphthalene obtained in Synthesis Example 2, 0.33 g of tetrakis(triphenylphosphine)palladium(0) (manufactured by TOKYO KASEI Co., Ltd.), 60 ml of 1,2-dimethoxyethane (manufactured by HIROSHIMA WAKO Co., Ltd.) and 4.55 g of sodium carbonate (manufactured by HIROSHIMA WAKO Co., Ltd.) into 21 ml of water was placed into a 300 ml flask, and the resultant mixture was stirred for 24 hours while being heated under the refluxing condition. After the reaction was completed, the reaction mixture was cooled to the room temperature, and formed crystals were separated by filtration. The obtained compound was purified in accordance with the column chromatography, and 3.6 g of a light yellow solid substance was obtained Since m/z=580 in FD-MS of the obtained compound, which corresponded to $C_{46}H_{28}$=580, the compound was identified to be AN28 (the yield: 43%).

Example 4

Synthesis of a Compound (AN30)

Under the atmosphere of argon, a solution prepared by dissolving 7.24 g of 10-(3-fluoranthenyl)anthracene-9-boric acid obtained in Synthesis Example 4, 5.13 g of 3-(4-bromophenyl)fluoranthene obtained in Synthesis Example 3, 0.33 g of tetrakis(triphenylphosphine)palladium(0) (manufactured by TOKYO KASEI Co., Ltd.), 60 ml of 1,2-dimethoxyethane (manufactured by HIROSHIMA WAKO Co., Ltd.) and 4.55 g of sodium carbonate (manufactured by HIROSHIMA WAKO Co., Ltd.) into 21 ml of water was placed into a 300 ml flask, and the resultant mixture was stirred for 24 hours while being heated under the refluxing condition. After the reaction was completed, the reaction mixture was cooled to the room temperature, and formed crystals were separated by filtration. The obtained compound was purified in accordance with the column chromatography, and 3.1 g of a light yellow solid substance was obtained Since m/z=654 in FD-MS of the obtained compound, which corresponded to $C_{52}H_{30}$=654, the compound was identified to be AN30 (the yield: 33%).

Example 5

Preparation of an Organic EL Device

A glass substrate (manufactured by GEOMATEC Company) of 25 mm×75 mm×1.1 mm thickness having an ITO transparent electrode was cleaned by application of ultrasonic wave in isopropyl alcohol for 5 minutes and then by exposure to ozone generated by ultraviolet light for 30 minutes. The glass substrate having the transparent electrode lines which had been cleaned was attached to a substrate holder of a vacuum vapor deposition apparatus. On the surface of the cleaned substrate at the side having the transparent electrode, a film of N,N'-bis(N,N'-diphenyl-4-aminophenyl)-N,N-diphenyl-4,4'-diamino-1,1'-biphenyl shown below (referred to as a film of TPD232, hereinafter) having a thickness of 60 nm was formed in a manner such that the formed film covered the transparent electrode. The formed film of TPD232 worked as the hole injecting layer. On the formed film of TPD232, a film of N,N,N',N'-tetra (4-biphenyl)diaminobiphenylene shown below (referred to as a film of TBDB, hereinafter) having a thickness of 20 nm was formed. The formed film of TBDB worked as the hole transporting layer. On the formed film of TBDB, a film of the compound AN8 as the light emitting material having a thickness of 40 nm was formed by vapor deposition. At the same time, an amine compound D1 having styryl group which is shown below was vapor deposited as the light emitting material in an amount such that the relative amounts by weight of AN8: D1 was 40:2. The formed film worked as the light emitting layer. On the film formed above, a film of Alq shown below having a thickness of 10 nm was formed. The film of Alq worked as the electron injecting layer. Thereafter, Li (the source of lithium: manufactured by SAES GETTERS Company) as the reducing dopant and Alq were binary vapor deposited, and an Alq:Li film (the thickness: 10 nm) was formed as the electron injecting layer (cathode). On the formed Alq:Li film, metallic aluminum was vapor deposited to form a metal cathode, and an organic EL device was prepared.

Using the obtained organic EL device, the efficiency of light emission and the half life at an initial luminance of 1,000 nit under the ordinary environment of the use were measured. The results are shown in Table 1.

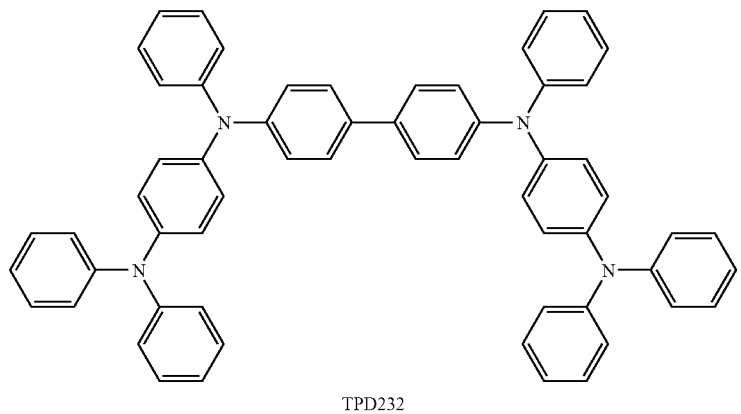

TPD232

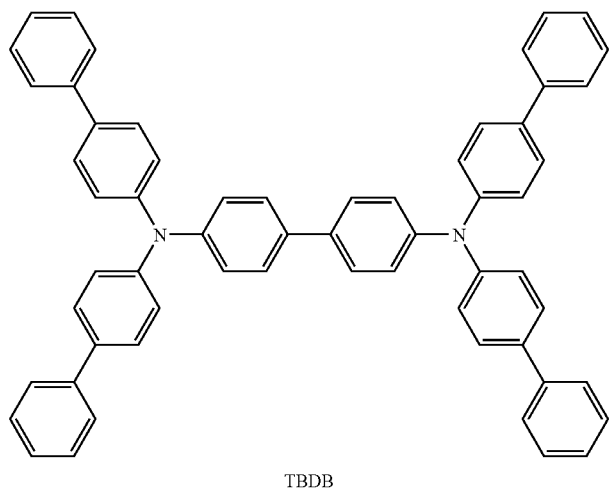

TBDB

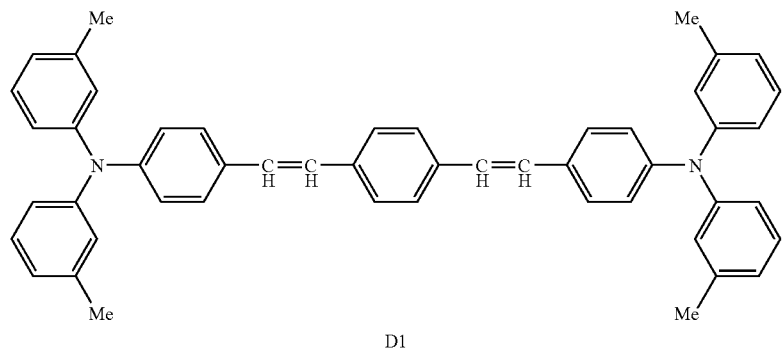

D1

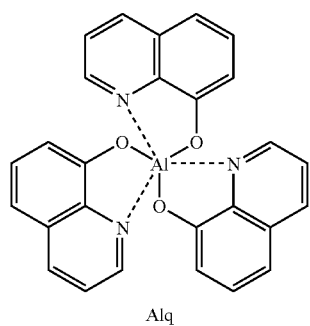

Alq

Examples 6 to 8

Preparation of Organic EL Devices

Organic EL devices were prepared in accordance with the same procedures as those conducted in Example 5 except that compounds shown in Table 1 were used as the light emitting material in place of AN8, and the efficiency of light emission and the half life at an initial luminance of 1,000 nit under the ordinary environment of the use were measured. The results are shown in Table 1.

Example 9

Preparation of an Organic EL Device

An organic EL device was prepared in accordance with the same procedures as those conducted in Example 5 except that an aromatic amine D2 shown below was used as the light emitting material in place of the amine compound having styryl group D1, and the efficiency of light emission and the half life at an initial luminance of 1,000 nit under the ordinary environment of the use were measured. The results are shown in Table 1.

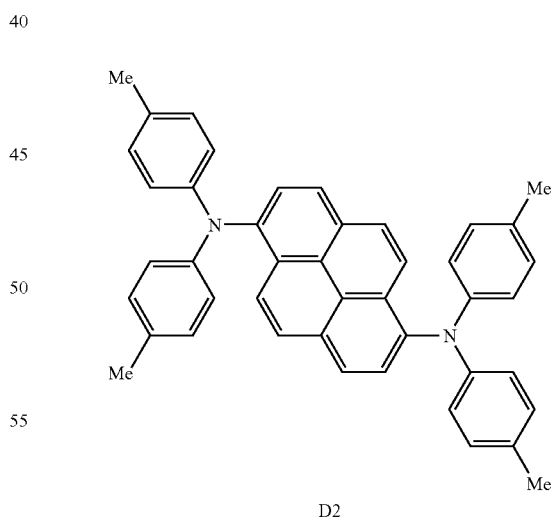

D2

Example 10

Synthesis of a Compound (AN5)

The same procedures as those conducted in Example 1 were conducted except that 3,5-diphenylbromobenzene was used in place of 2-(4-bromophenyl)naphthalene, and 5.6 g of a light yellow solid substance was obtained.

Since m/z=532 in FD-MS of the obtained compound, which corresponded to $C_{42}H_{28}Br=532$, the compound was identified to be AN5 (the yield: 45%).

Example 11

Synthesis of a Compound (AN7)

The same procedures as those conducted in Example 1 were conducted except that 1-(4-bromophenyl)naphthalene was used in place of 2-(4-bromophenyl)naphthalene, and 7.8 g of a light yellow solid substance was obtained.

Since m/z=506 in FD-MS of the obtained compound, which corresponded to $C_{40}H_{26}Br=506$, the compound was identified to be AN7 (the yield: 54%).

Example 12

Synthesis of a Compound (AN49)

The same procedures as those conducted in Example 1 were conducted except that 2-(3-bromophenyl)naphthalene was used in place of 2-(4-bromophenyl)naphthalene, and 6.9 g of a light yellow solid substance was obtained.

Since m/z=506 in FD-MS of the obtained compound, which corresponded to $C_{40}H_{26}Br=506$, the compound was identified to be AN49 (the yield: 52%).

Examples 13 to 15

Preparation of Organic EL Devices

Organic EL devices were prepared in accordance with the same procedures as those conducted in Example 5 except that compounds shown in Table 1 were used as the light emitting material in place of AN8, and the efficiency of light emission and the half life at an initial luminance of 1,000 nit under the ordinary environment of the use were measured. The results are shown in Table 1.

Comparative Example 1

Preparation of an Organic EL Device

An organic EL device was prepared in accordance with the same procedures as those conducted in Example 5 except that an1 shown below was used as the light emitting material in place of AN8, and the efficiency of light emission and the half life at an initial luminance of 1,000 nit under the ordinary environment of the use were measured. The results are shown in Table 1.

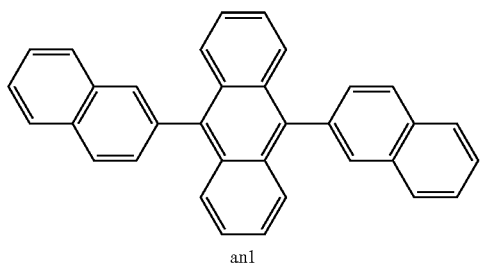

an1

Comparative Example 2

Preparation of an Organic EL Device

An organic EL device was prepared in accordance with the same procedures as those conducted in Example 5 except that an2 shown below was used as the light emitting material in place of AN8, and the efficiency of light emission and the half life at an initial luminance of 1,000 nit under the ordinary environment of the use were measured. The results are shown in Table 1.

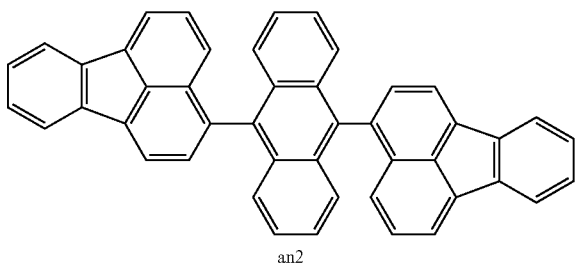

an2

TABLE 1

| | Compounds of light emitting layer | Efficiency of light emission (cd/A) | Half life (hour) | Color of emitted light |
|---|---|---|---|---|
| Example 5 | AN8/D1 | 11.2 | 4,200 | blue |
| Example 6 | AN10/D1 | 11.0 | 4,000 | blue |
| Example 7 | AN28/D1 | 10.9 | 3,700 | blue |
| Example 8 | AN30/D1 | 10.8 | 3,700 | blue |
| Example 9 | AN8/D2 | 10.6 | 3,200 | blue |
| Example 13 | AN5/D1 | 11.0 | 2,200 | blue |
| Example 14 | AN7/D1 | 11.3 | 4,500 | blue |
| Example 15 | AN49/D1 | 11.3 | 4,500 | blue |
| Comparative Example 1 | an1/D1 | 9.0 | 2,200 | blue |
| Comparative Example 2 | an2/D1 | 8.8 | 1,100 | blue |

As shown in Table 1, the organic EL devices of Examples 5 to 9 and 13 to 15 exhibited great efficiencies of light emission and had very long lives. In contrast, the organic EL devices of Comparative Examples 1 and 2 exhibited small efficiencies of light emission and had short lives.

INDUSTRIAL APPLICABILITY

As described in detail in the above, the organic EL device of the present invention and the organic EL device using the anthracene derivative of the present invention exhibit great efficiencies of light emission, have long lives and, therefore, are advantageously used as the organic EL device which is considered to be used continuously for a long time.

The invention claimed is:
1. An electroluminescence device which comprises:
a cathode,
an anode and
an organic thin film layer comprising at least one layer comprising a light emitting layer and disposed between the cathode and the anode,
wherein
the light emitting layer comprises a light emitting material comprising at least one anthracene derivative represented by general formula (2)

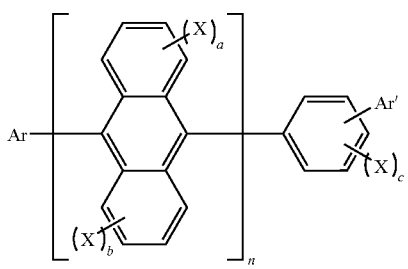

(2)

wherein Ar is a condensed aromatic group selected from the group consisting of 1-naphthyl group, 2-naphthyl group, 1-anthryl group, 2-anthryl group, 1-phenanthryl group, 2-phenanthryl group, 3-phenanthryl group, 4-phenanthryl group, 1-naphthacenyl group, 2-naphthacenyl group, 9-naphthacenyl group, 1-pyrenyl group, 2-pyrenyl group, 4-pyrenyl group and fluoranthenyl group, each being optionally substituted;

Ar' is an aromatic group selected from the group consisting of a 1-naphthyl group, a 2-naphthyl group, a 1-anthryl group, a 2-anthryl group, a 1-phenanthryl group, a 2-phenanthryl group, a 3-phenanthryl group, a 4-phenanthryl group, a 1-naphthacenyl group, a 2-naphthacenyl group, a 9-naphthacenyl group, a 1-pyrenyl group, a 2-pyrenyl group, a 4-pyrenyl group and a fluoranthenyl group, each being optionally substituted;

X represents a hydrogen or an aromatic group having 6 to 50 nuclear carbon atoms;

a and b each represent an integer of 0 to 4; and n represents an integer of 1 to 3 and, when n represents 2 or 3, two or three groups represented by:

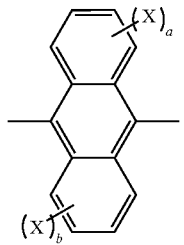

may be a same with or different from each other.

2. The electroluminescence device according to claim 1, wherein the group represented by Ar in general formula (2) is a group selected from groups represented by following general formulae

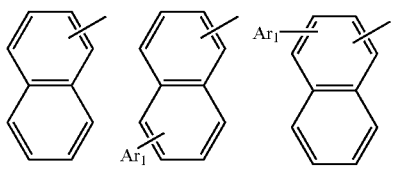

wherein $Ar_1$ represents a substituted or unsubstituted aromatic group having 6 to 50 nuclear carbon atoms.

3. The electroluminescence device according to claim 1, wherein the light emitting layer further comprises an arylamine compound.

4. The electroluminescence device according to claim 1, wherein the light emitting layer further comprises a styrylamine compound.

5. The electroluminescence device according to claim 1, wherein X is hydrogen.

6. The electroluminescence device according to claim 1, wherein n is 1.

7. The electroluminescence device according to claim 1, wherein X is hydrogen and n is 1.

* * * * *

UNITED STATES PATENT AND TRADEMARK OFFICE
CERTIFICATE OF CORRECTION

PATENT NO. : 7,839,074 B2
APPLICATION NO. : 10/524825
DATED : November 23, 2010
INVENTOR(S) : Hidetsugu Ikeda et al.

Page 1 of 1

It is certified that error appears in the above-identified patent and that said Letters Patent is hereby corrected as shown below:

Please amend Claim 1, by replacing the formula (2) shown in Col. 45, lines 1-12 (Claim 1) with the formula (2) shown in Col. 3, lines 20-30.

Delete formula (2) at Column 45, lines 1-12 in its entirety and replace with the following

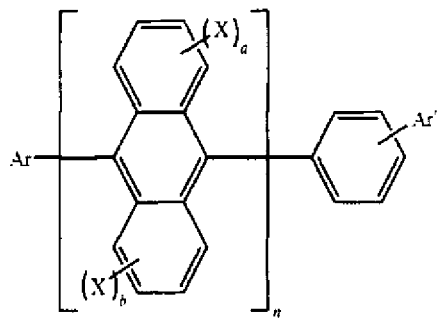

--                                    --

Signed and Sealed this
Tenth Day of April, 2012

David J. Kappos
*Director of the United States Patent and Trademark Office*